United States Patent [19]

Fujikawa et al.

[11] Patent Number: 5,102,888
[45] Date of Patent: Apr. 7, 1992

[54] QUINOLINE TYPE MEVALONOLACTONES USEFUL FOR TREATING HYPERLIPIDEMIA AND RELATED DISEASES

[75] Inventors: Yoshihiro Fujikawa; Mikio Suzuki; Hiroshi Iwasaki, all of Funabashi; Mitsuaki Sakashita; Masaki Kitahara, both of Shiraoka, all of Japan

[73] Assignee: Nissan Chemical Industries Ltd., Tokyo, Japan

[21] Appl. No.: 483,724

[22] Filed: Feb. 23, 1990

Related U.S. Application Data

[62] Division of Ser. No. 233,752, Aug. 19, 1988.

[30] Foreign Application Priority Data

Aug. 20, 1987 [JP] Japan .................. 62-207224
Jan. 26, 1988 [JP] Japan .................. 63-15585

[51] Int. Cl.⁵ .............. C07D 491/048; C07D 491/056; A61K 31/44
[52] U.S. Cl. ........................ 514/291; 546/90; 546/14; 514/63
[58] Field of Search .............. 546/90, 14; 514/291, 514/63

[56] References Cited

U.S. PATENT DOCUMENTS 4,761,419 8/1988 Picard et al. ................ 514/311

FOREIGN PATENT DOCUMENTS 0114027 7/1984 European Pat. Off. ............ 548/517
0179559 4/1986 European Pat. Off. ............ 548/517
WO86/00307 1/1986 PCT Int'l Appl. ................ 548/374

Primary Examiner—Alan L. Rotman
Attorney, Agent, or Firm—Oblon, Spivak, McClelland, Maier & Neustadt

[57] ABSTRACT

A compound of the formula:

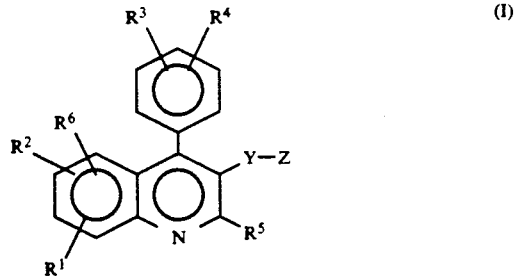

wherein $R^1$, $R^2$, $R^3$, $R^4$ and $R^6$ are independently hydrogen, $C_{1-6}$ alkyl, $C_{1-6}$ cycloalkyl, $C_{1-3}$ alkoxy, n-botoxy, i-botoxy, sec-butoxy, $R^7R^8N-$ (wherein $R^7$ and $R^8$ are independently hydrogen or $C_{1-3}$ alkyl), trifluoromethyl, trifluoromethoxy, difluoromethoxy, fluoro, chloro, bromo, phenyl, phenoxy, benzyloxy, hydroxy, trimethylsilyloxy, diphenyl-t-butylsilyloxy, hydroxymethyl or $-O(CH_2)_lOR^{19}$ (wherein $R^{19}$ is hydrogen or $C_{1-3}$ alkyl, and l is 1,2 or 3); or when located at the ortho position to each other, $R^1$ and $R^2$, or $R^3$ and $R^4$ together form $-CH=CH-CH=CH-$; or when located at the ortho position to each other, $R^1$ and $R^2$ together form $-OC(R^{15})(R^{16})O-$ (wherein $R^{15}$ and $R^{16}$ are independently hydrogen or $C_{1-3}$ alkyl); Y is $-CH_2-$, $-CH_2CH_2-$, $-CH=CH-$, $-CH_2-CH=CH-$ or $-CH=CH-CH_2-$; and Z is $-Q-CH_2WCH_2-CO_2R^{12}$,

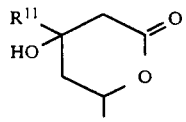 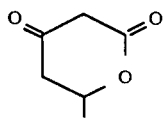

or

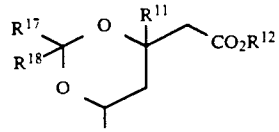

(wherein Q is $-C(O)-$, $-C(OR^{13})_2-$ or $-CH(OH)-$; W is $-C(O)-$, $-C(OR^{13})_2-$ or $-C(R^{11})(OH)-$; $R^{11}$ is hydrogen atom or $C_{1-3}$ alkyl; $R^{12}$ is hydrogen or $R^{14}$ (wherein $R^{14}$ is physiologically hydrolyzable alkyl or M (wherein M is $NH_4$, sodium, potassium, ½ calcium or a hydrate of lower alkyl amine, di-lower alkyl amine or tri-lower alkyl amine)); two $R^{13}$ are independently primary or secondary $C_{1-6}$ alkyl; or two $R^{13}$ together form $-(CH_2)_2-$ or $-(CH_2)_3-$; $R^{17}$ and $R^{18}$ are independently hydrogen or $C_{1-3}$ alkyl; and $R^5$ is hydrogen, $C_{1-6}$ alkyl, $C_{2-3}$ alkenyl, $C_{3-6}$ cycloalkyl,

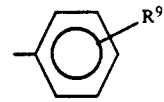

wherein $R^9$ is a hydrogen atom, $C_{1-4}$ alkyl, $C_{1-3}$ alkoxy, fluoro, chloro, bromo or trifluoromethyl), phenyl-$(CH_2)_m-$ (wherein m is 1,2 or 3), $-(CH_2)_nCH(CH_3)-$phenyl or phenyl—$(CH_2)_nCH(CH_3)-$ (wherein n is 0,1 or 2).

12 Claims, No Drawings

QUINOLINE TYPE MEVALONOLACTONES USEFUL FOR TREATING HYPERLIPIDEMIA AND RELATED DISEASES

This is a division of application Ser. No. 07/233,752, filed on Aug. 19, 1988.

The present invention relates to novel mevalonolactones having a quinoline ring, processes for their production, pharmaceutical compositions containing them and their pharmaceutical uses particularly as anti-hyperlipidemic, hypolipoproteinemic and anti-antherosclerotic agents, and intermediates useful for their production and processes for the production of such intermediates.

Some fermentation metabolic products such as compactine, CS-514, Mevinolin or semi-synthetic derivatives or fully synthetic derivatives thereof are known to be inhibitors against HMG-CoA reductase which is a rate limiting enzyme for cholesterol biosynthesis. (A. Endo J. Med Chem., 28(4) 401 (1985))

CS-514 and Mevinolin have been clinically proved to be potentially useful anti-hyperlipoproteinemic agents, and they are considered to be effective for curing or preventing diseases of coronary artery sclerosis or atherosclerosis. (IXth Int. Symp. Drugs Affect. Lipid Metab., 1986, p30, p31, p66)

However, with respect to fully synthetic derivatives, particularly hetero aromatic derivatives of inhibitors against HMG—CoA reductase, limited information is disclosed in the following literatures:

WPI ACC NO. 84-158675, 86-028274, 86-098816, 86-332070, 87-124519, 87-220987, 88-07781, 88-008460, 88-091798 and 88-112505.

The present inventors have found that mevalonolactone derivatives having a quinoline ring, the corresponding dihydroxy carboxylic acids and salts and esters thereof have high inhibitory activities against cholesterol biosynthesis wherein HMG—CoA reductase acts as a rate limiting enzyme. The present invention has been accomplished on the basis of this discovery.

The novel mevalonolactone derivatives of the present invention are represented by the following formula I:

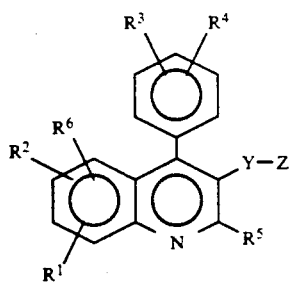

(I)

wherein $R^1$, $R^2$, $R^3$, $R^4$ and $R^6$ are independently hydrogen, $C_{1-6}$ alkyl, $C_{3-6}$ cycloalkyl, $C_{1-3}$ alkoxy, n-butoxy, i-butoxy, sec-butoxy, $R^7R^8N-$ (wherein $R^7$ and $R^8$ are independently hydrogen or $C_{1-3}$ alkyl), trifluoromethyl, trifluoromethoxy, difluoromethoxy, fluoro, chloro, bromo, phenyl, phenoxy, benzyloxy, hydroxy, trimethylsilyloxy, diphenyl-t-butylsilyloxy, hydroxymethyl or $-O(CH_2)_lOR^{19}$ (wherein $R^{19}$ is hydrogen or $C_{1-3}$ alkyl, and l is 1, 2 or 3); or when located at the ortho position to each other, $R^1$ and $R^2$, or $R^3$ and $R^4$ together optionally form $-CH=CH-CH=CH-$; or when located at the ortho position to each other, $R^1$ and $R^2$ together optionally form $-OC(R^{15})(R^{16})O-$ (wherein $R^{15}$ and $R^{16}$ are independently hydrogen or $C_{1-3}$ alkyl); Y is $-CH_2-$, $-CH_2CH_2-$, $-CH=CH-$, $-CH_2-CH=CH-$ or $-CH=CH-CH_2-$; and Z is $-Q-CH_2WCH_2-CO_2R^{12}$,

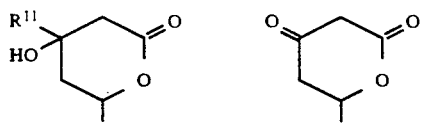

or

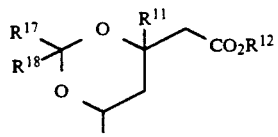

(wherein Q is $-C(O)-$, $-C(OR^{13})_2-$ or $-CH(OH)-$; W is $-C(O)-$, $-C(OR^{13})_2-$ or $-C(R^{11})(OH)-$; $R^{11}$ is hydrogen or $C_{1-3}$ alkyl; $R^{12}$ is hydrogen or $R^{14}$ (wherein $R^{14}$ is physiologically hydrolyzable alkyl or M (wherein M is $NH_4$, sodium, potassium, ½ calcium or a hydrate of lower alkylamine, di-lower alkylamine or tri-lower alkylamine)); two $R^{13}$ are independently primary or secondary $C_{1-6}$ alkyl; or two $R^{13}$ together form $-(CH_2)_2-$ or $-(CH_2)_3-$; $R^{17}$ and $R^{18}$ are independently hydrogen or $C_{1-3}$ alkyl; and $R^5$ is hydrogen, $C_{1-6}$ alkyl, $C_{2-3}$ alkenyl, $C_{3-6}$ cycloalkyl,

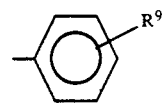

(wherein $R^9$ is hydrogen, $C_{1-4}$ alkyl, $C_{1-3}$ alkoxy, fluoro, chloro, bromo or trifluoromethyl), phenyl$-(CH_2)_m-$ (wherein m is 1, 2 or 3), $-(CH_2)_nCH(CH_3)$-phenyl or phenyl-$(CH_2)_nCH(CH_3)-$ (wherein n is 0, 1 or 2).

Various substituents in the formula I will be described in detail with reference to specific examples. However, it should be understood that the present invention is by no means restricted by such specific examples.

$C_{1-6}$ alkyl for $R^1$, $R^2$, $R^3$, $R^4$, $R^6$ and $R^9$ includes, for example, methyl, ethyl, n-propyl, i-propyl, n-butyl, i-butyl, sec-butyl and t-butyl. $C_{1-3}$ alkoxy for $R^1$, $R^2$, $R^3$, $R^4$ and $R^6$ includes, for example, methoxy, ethoxy, n-propoxy and i-propoxy.

$C_{1-3}$ alkyl for $R^{11}$ includes, for example, methyl, ethyl, n-propyl and i-propyl.

$C_{1-3}$ alkyl for $R^{13}$ includes, for example, methyl, ethyl, n-propyl and i-propyl.

Alkyl for $R^{14}$ includes, for example, methyl, ethyl, n-propyl, i-propyl, n-butyl and i-butyl.

M is a metal capable of forming a pharmaceutically acceptable salt, and it includes, for example, sodium and potassium.

$CO_2M$ includes, for example, $-CO_2NH_4$ and $-CO_2H$ (primary to tertiary lower alkylamine such as trimethylamine).

$C_{1-6}$ alkyl for $R^5$ includes, for example, methyl, ethyl, n-propyl, i-propyl, n-butyl, i-butyl, sec-butyl, t-butyl, n-pentyl and n-hexyl.

$C_{3-6}$ cycloalkyl for $R^5$ includes, for example, cyclopropyl, cyclobutyl, cyclopentyl and cyclohexyl.

$C_{2-3}$ alkenyl for $R^5$ includes, for example, vinyl and i-propenyl.

Phenyl-$(CH_2)_m$— for $R^5$ includes, for example, benzyl, β-phenylethyl and γ-phenylpropyl.

Phenyl-$(CH_2)_n CH(CH_3)$— for $R^5$ includes, for example, α-phenylethyl and α-benzylethyl.

$C_{1-3}$ alkyl for $R^7$ and $R^8$ includes, for example, methyl, ethyl, n-propyl and i-propyl.

Further, these compounds may have at least one or two asymmetric carbon atoms and may have at least two to four optical isomers. The compounds of the formula I include all of these optical isomers and all of the mixtures thereof.

Among compounds having carboxylic acid moieties falling outside the definition of $-CO_2R^{12}$ of the carboxylic acid moiety of substituent Z of the compounds of the present invention, those which undergo physiological hydrolysis, after intake, to produce the corresponding carboxylic acids (compounds wherein the $-CO_2R^{12}$ moiety is $-CO_2H$) are equivalent to the compounds of the present invention.

Now, preferred substituents of the compounds of the present invention will be described.

In the following preferred, more preferred still further preferred and most preferred examples, the numerals for the positions of the substituents indicate the positions on the quinoline ring. For example, N' shown by e.g. 1' or 2' indicates the position of the substituent on the phenyl substituted at the 4-position of the quinoline ring (the carbon connected to the quinoline ring is designated as 1'). The meanings of the respective substituents are the same as the above-mentioned meanings.

Preferred substituents for $R^1$, $R^2$ and $R^6$ are hydrogen, fluoro, chloro, bromo, $C_{1-3}$ alkyl, $C_{1-3}$ alkoxy, $C_{3-6}$ cycloalkyl, dimethylamino, hydroxy, hydroxymethyl, hydroxyethyl, trifluoromethyl, trifluoromethoxy, difluoromethoxy, phenoxy and benzyloxy.

Further, when $R^6$ is hydrogen, it is preferred that $R^1$ and $R^2$ together form methylenedioxy.

As preferred examples for $R^3$ and $R^4$, when $R^4$ is hydrogen, $R^3$ is hydrogen, 3'-fluoro, 3'-chloro, 3'-methyl, 4'-methyl, 4'-chloro and 4'-fluoro.

Other preferred combinations of $R^3$ and $R^4$ include 3'-methyl-4'-chloro, 3',5'-dichloro, 3',5'-difluoro, 3',5'-dimethyl and 3'-methyl-4'-fluoro.

Preferred examples for $R^5$ include primary and secondary $C_{1-6}$ alkyl and $C_{3-6}$ cycloalkyl.

Preferred examples for Y include $-CH_2-CH_2-$ and $-CH=CH-$.

Preferred examples for Z include

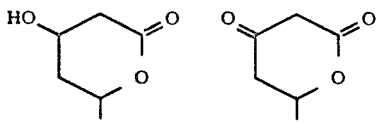

$-CH(OH)CH_2CH_2(OH)CH_2CO_2R^{12}$, $-CH(OH)CH_2C(O)CH_2CO_2R^{12}$ and $-CH(OH)CH_2C(OR^{13})_2CH_2CO_2R^{12}$.

Now, more preferred substituents of the compounds of the present invention will be described.

As more preferred examples for $R^1$, $R^2$ and $R^6$, when both $R^2$ and $R^6$ are hydrogen, $R^1$ is hydrogen, 5-fluoro, 6-fluoro, 7-fluoro, 8-fluoro, 5-chloro, 6-chloro, 7-chloro, 8-chloro, 5-bromo, 6-bromo, 7-bromo, 8-bromo, 5-methyl, 6-methyl, 7-methyl, 8-methyl, 5-methoxy, 6-methoxy, 7-methoxy, 8-methoxy, 5trifluoromethyl, 6-trifluoromethyl, 7-trifluoromethyl, 8-trifluoromethyl, 6-trifluoromethoxy, 6-difluoromethoxy, 8-hydroxyethyl, 5-hydroxy, 6-hydroxy, 7-hydroxy, 8-hydroxy, 6-ethyl, 6-n-butyl and 7-dimethylamino.

When $R^6$ is hydrogen, $R^1$ and $R^2$ together represent 6-chloro-8-methyl, 6-bromo-7-methoxy, 6-methyl-7-chloro, 6-chloro-8-hydroxy, 5-methyl-2-hydroxy, 6-methoxy-7-chloro, 6-chloro-7-methoxy, 6-hydroxy-7-chloro, 6-chloro-7-hydroxy, 6-chloro-8-bromo, 5-chloro-6-hydroxy, 6-bromo-8-chloro, 6-bromo-8-hydroxy, 5-methyl-8-chloro, 7-hydroxy-8-chloro, 6-bromo-8-hydroxy, 6-methoxy-7-methyl, 6-chloro-8-bromo, 6-methyl-8-bromo, 6,7-difluoro, 6,8-difluoro, 6,7-methylenedioxy, 6,8-dichloro, 5,8-dimethyl, 6,8-dimethyl, 6,7-dimethoxy, 6,7-diethoxy, 6,7-dibromo or 6,8-dibromo.

When $R^1$, $R^2$ and $R^6$ are not hydrogen, they together represent 5,7-dimethoxy-8-hydroxy, 5,8-dichloro-6-hydroxy, 6,7,8-trimethoxy, 6,7,8-trimethyl, 6,7,8-trichloro, 5-fluoro-6,8-dibromo or 5-chloro-6,8-dibromo.

As more preferred examples for $R^3$ and $R^4$, when $R^3$ is hydrogen, $R^4$ is hydrogen, 4'-methyl, 4'-chloro or 4'-fluoro. When both $R^3$ and $R^4$ are not hydrogen, they together represent 3',5'-dimethyl or 3'-methyl-4'-fluoro.

As more preferred examples for $R^5$, the above-mentioned preferred examples of $R^5$ may be mentioned.

As preferred examples for Y, $-CH_2-CH_2-$ and (E)$-CH=CH-$ may be mentioned. As more preferred examples for Z, the above preferred examples for Z may be mentioned.

Now, still further preferred substituents of the compounds of the present invention will be described. As examples for $R^1$, $R^2$ and $R^6$, when both $R^2$ and $R^6$ are hydrogen, $R^1$ is hydrogen, 6-methyl, 6-ethyl, 6-trifluoromethyl, 6-hydroxy, 6-methoxy, 6-chloro, 6-bromo, 6-n-butyl and 7-dimethylamino.

When only $R^6$ is hydrogen, $R^1$ and $R^2$ represent 6,8-dichloro, 5,8-dimethyl, 6,8-dimethyl, 6,7-dimethoxy, 6,7-diethoxy, 6,7-dibromo, 6,8-dibromo, 6,7-difluoro and 6,8-difluoro.

As still further preferred examples for $R^3$ and $R^4$, when $R^3$ is hydrogen, $R^4$ is hydrogen, 4'-chloro or 4'-fluoro, or $R^3$ and $R^4$ together represent 3'-methyl-4'-fluoro.

Still further preferred examples for $R^5$ include ethyl, n-propyl, i-propyl and cyclopropyl.

Still further preferred examples for Y include (E)$-CH=CH-$.

As still further preferred examples for Z, the above-mentioned preferred example for Z may be mentioned.

Now, the most preferred substituents for the compounds of the present invention will be described.

As the most preferred examples for $R^1$, $R^2$ and $R^6$, when both $R^2$ and $R^6$ are hydrogen, $R^1$ is hydrogen, 6-methyl or 6-chloro.

When only $R^6$ is hydrogen, $R^1$ and $R^2$ together represent, for example, 6,7-dimethoxy.

As the most preferred examples for $R^3$ and $R^4$, $R^3$ is hydrogen and $R^4$ is hydrogen, 4'-chloro or 4'-fluoro.

The most preferred examples for $R^5$ include i-propyl and cyclopropyl. The most preferred example for Y may be (E)$-CH=CH-$.

As the most preferred examples for Z, the above-mentioned preferred examples for Z may be mentioned.

Now, particularly preferred specific compounds of the present invention will be presented. The following compounds (a) to (z) are shown in the form of carboxylic acids. However, the present invention include not only the compounds in the form of carboxylic acids but also the corresponding lactones formed by the condensation of the carboxylic acids with hydroxy at the 5-position, and sodium salts and lower alkyl esters (such as methyl, ethyl, i-propyl and n-propyl esters) of the carboxylic acids, which can be physiologically hydrolyzed to the carboxylic acids.

(a) (E)-3,5-dihydroxy-7-[4'-(4''-fluorophenyl)-2'-(1''-methylethyl)-quinolin-3'-yl]-hept-6-enoic acid (b) (E)-3,5-dihydroxy-7-[4'-(4''-fluorophenyl)-2'-(1''-methylethyl)-6'-chloro-quinolin-3'-yl]-hept-6-enoic acid (c) (E)-3,5-dihydroxy-7-[4'-(4''-fluorophenyl)-2'-(1''-methylethyl)-6'-methyl-quinolin-3'-yl]-hept-6-enoic acid (d) (E)-3,5-dihydroxy-7-[4'-(4''-fluorophenyl)-2'-(1''-methylethyl)-6',7'-dimethoxy-quinolin-3'-yl]-hept-6-enoic acid (e) (E)-3,5-dihydroxy-7-[4'-(4''-fluorophenyl)-2'-cyclopropyl-quinolin-3'-yl]-hept-6-enoic acid (f) (E)-3,5-dihydroxy-7-[4'-(4''-fluorophenyl)-2'-cyclopropyl-6'-chloro-quinolin-3'-yl]-hept-6-enoic acid (g) (E)-3,5-dihydroxy-7-[4'-(4''-fluorophenyl)-2'-cyclopropyl-6'-methyl-quinolin-3'-yl]-hept-6-enoic acid (h) (E)-3,5-dihydroxy-7-[4'-(4''-fluorophenyl)-2'-cyclopropyl-6',7'-dimethoxy-quinolin-3'-yl]-hept-6-enoic acid (i) (E)-3,5-dihydroxy-7-[4'-(4''-chlorophenyl)-2'-(1''-methylethyl)-quinolin-3'-yl]-hept-6-enoic acid (j) (E)-3,5-dihydroxy-7-[4'-(4''-chlorophenyl)-2'-(1''-methylethyl)-6'-chloro-quinolin-3'-yl]-hept-6-enoic acid (k) (E)-3,5-dihydroxy-7-[4'-(4''-chlorophenyl)-2'-(1''-methylethyl)-6'-methyl-quinolin-3'-yl]-hept-6-enoic acid (l) (E)-3,5-dihydroxy-7-[4'-(4''-chlorophenyl)-2'-(1''-methylethyl)-6',7'-dimethoxy-quinolin-3'-yl]-hept-6-enoic acid (m) (E)-3,5-dihydroxy-7-[4'-(4''-chlorophenyl)-2'-cyclopropyl-quinolin-3'-yl]-hept-6-enoic acid (n) (E)-3,5-dihydroxy-7-[4'-(4''-chlorophenyl)-2'-cyclopropyl-6'-chloro-quinolin-3'-yl]-hept-6-enoic acid (o) (E)-3,5-dihydroxy-7-[4'-(4''-chlorophenyl)-2'-cyclopropyl-6'-methyl-quinolin-3'-yl]-hept-6-enoic acid (p) (E)-3,5-dihydroxy-7-[4'-(4''-chlorophenyl)-2'-cyclopropyl-6'7'-dimethoxy-quinolin-3'-yl]-hept-6-enoic acid (q) (E)-3,5-dihydroxy-7-[4'-phenyl-2'-(1''-methylethyl)-quinolin-3'-yl]-hept-6-enoic acid (r) (E)-3,5-dihydroxy-7-[4'-phenyl-2'-(1''-methylethyl)-6'-chloro-quinolin-3'-yl]-hept-6-enoic acid (s) (E)-3,5-dihydroxy-7-[4'-phenyl-2'-(1''-methylethyl)-6'-methyl-quinolin-3'-yl]-hept-6-enoic acid (t) (E)-3,5-dihydroxy-7-[4'-phenyl-2'-(1''-methylethyl)-6',7'-dimethoxy-quinolin-3'-yl]-hept-6-enoic acid (u) (E)-3,5-dihydroxy-7-[4'-phenyl-2'-cyclopropyl-quinolin-3'-yl]-hept-6-enoic acid (v) (E)-3,5-dihydroxy-7-[4'-phenyl-2'-cyclopropyl-6'-chloro-quinolin-3'-yl]-hept-6-enoic acid (w) (E)-3,5-dihydroxy-7-[4'-phenyl-2'-cyclopropyl-6'-methyl-quinolin-3'-yl]-hept-6-enoic acid (x) (E)-3,5-dihydroxy-7-[4'-phenyl-2'-cyclopropyl-6',7'-dimethoxy-quinolin-3'-yl]-hept-6-enoic acid (y) (E)-3,5-dihydroxy-7-[4'-(4''-fluorophenyl)-2'-(1''-methylethyl)-6'-methoxy-quinolin-3'-yl]-hept-6-enoic acid (z) (E)-3,5-dihydroxy-7-[4'-(4''-fluorophenyl)-2'-cyclopropyl-6'-methoxy-quinolin-3'-yl]-hept-6-enoic acid The mevalonolactones of the formula I can be prepared by the following reaction scheme. The enal III can also be prepared by processes K, L and M.

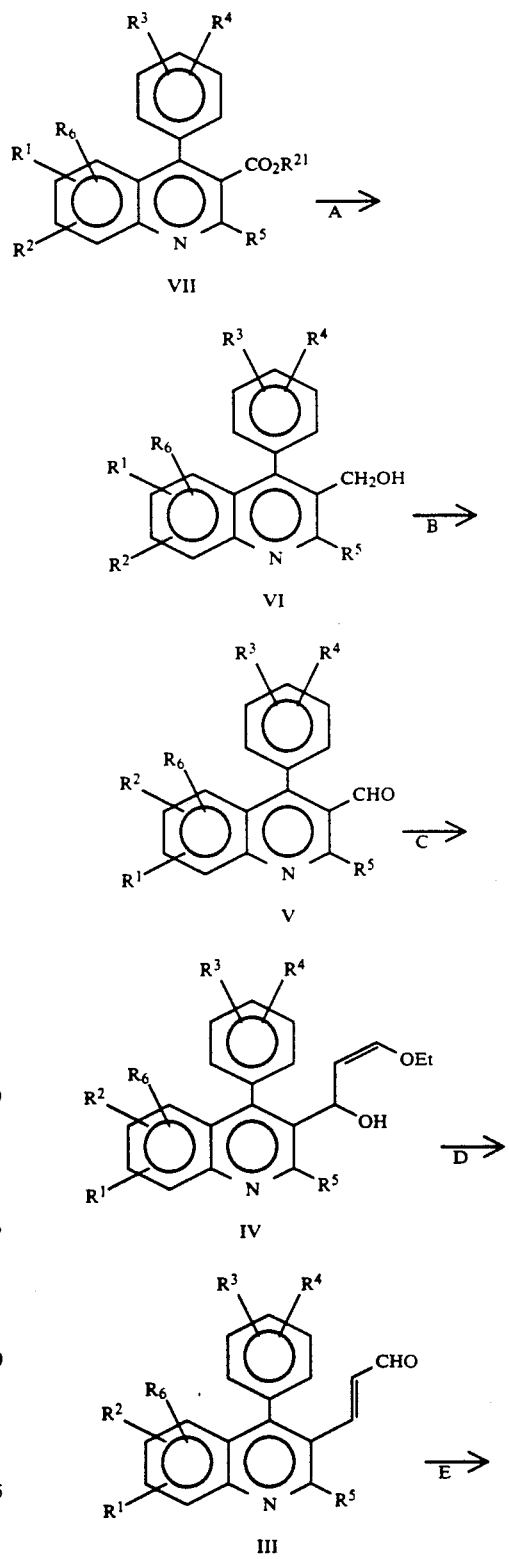

-continued
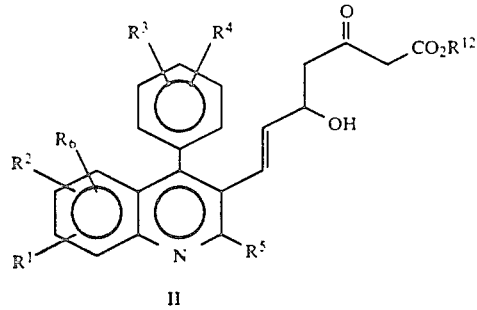
II
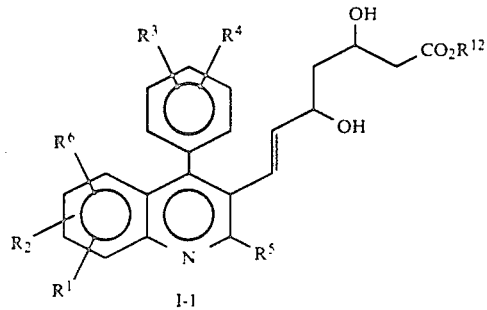
I-1
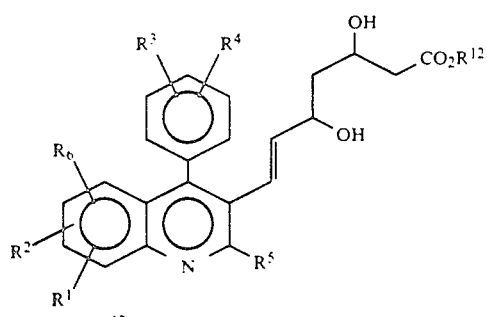
I-2 (R$^{12}$ = H)
I-5 (R$^{12}$ = Na)
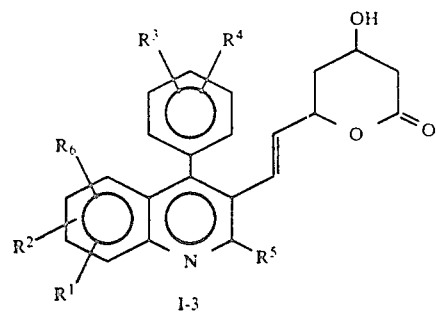
I-3
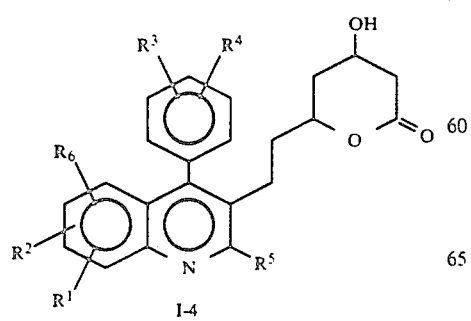
I-4
-continued
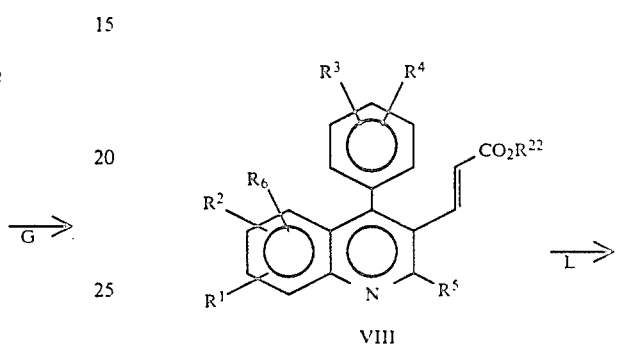
V
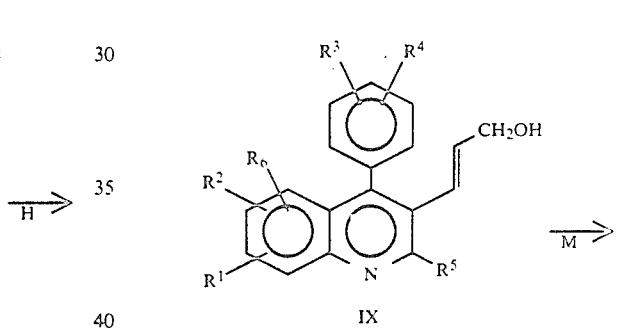
VIII
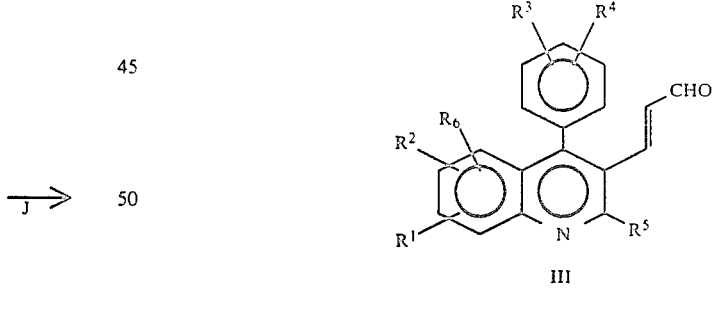
IX
III
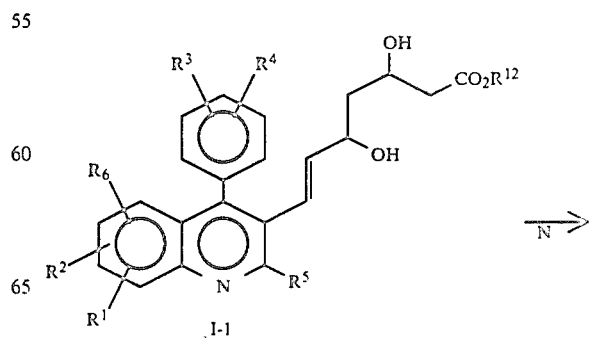
I-1

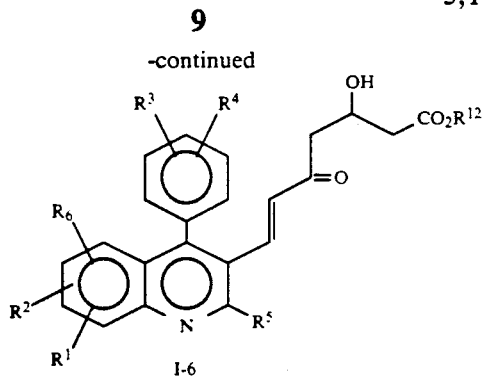

I-6

In the above reaction scheme, $R^1$, $R^2$, $R^3$, $R^4$, $R^5$, $R^6$ and $R^{12}$ are as defined above with respect to the formula I, and $R^{21}$ and $R^{22}$ independently represent $C_{1-4}$ lower alkyl such as methyl, ethyl, n-propyl, i-propyl or n-butyl.

Step A represents a reduction reaction of the ester to a primary alcohol. Such reduction reaction can be conducted by using various metal hydrides, preferably diisobutylaluminium hydride, in a solvent such as tetrahydrofuran or toluene at a temperature of from −20° to 20° C., preferably from −10° to 10° C.

Step B represents an oxidation reaction of the primary alcohol to an aldehyde, which can be conducted by using various oxidizing agents. Preferably, the reaction can be conducted by using pyridinium chlorochromate in methylene chloride at a temperature of from 0° to 25° C., or by using oxalyl chloride, dimethyl sulfoxide and a tertiary amine such as triethylamine (Swern oxidation), or by using a sulfur trioxide pyridine complex.

Step C represents a synthesis of a 3-ethoxy-1-hydroxy-2-propene derivative, which can be prepared by reacting a compound V to lithium compound which has been preliminarily formed by treating cis-1-ethoxy-2-(tri-n-butylstannyl)ethylene with butyl lithium in tetrahydrofuran.

As the reaction temperature, it is preferred to employ a low temperature at a level of from −60° to −78° C.

Step D represents a synthesis of an enal by acidic hydrolysis. As the acid catalyst, it is preferred to employ p-toluene sulfonic acid, hydrochloric acid or sulfuric acid, and the reaction may be conducted in a solvent mixture of water and tetrahydrofuran or ethanol at a temperature of from 10° to 25° C. The 3-ethoxy-1-hydroxy-2-propene derivative obtained in Step C can be used in Step D without purification i.e. by simply removing tetra-n-butyl tin formed simultaneously.

Step E represents a double anion condensation reaction between the enal III and an acetoacetate. Such condensation reaction is preferably conducted by using sodium hydride and n-butyl lithium as the base in tetrahydrofuran at a temperature of from −80° to 0° C., preferably from −30° to −10° C.

Step F represents a reduction reaction of the carbonyl group, which can be conducted by using a metal hydride, preferably sodium borohydride in ethanol at a temperature of from −10° to 25° C., preferably from −10° to 5° C.

Further, the reduction reaction may be conducted by using zinc borohydride in dry ethyl ether or dry tetrahydrofuran at a temperature of −100° to 25° C., preferably from −80° to −50° C.

Step G is a step for hydrolyzing the ester. The hydrolysis can be conducted by using an equimolar amount of a base, preferably potassium hydroxide or sodium hydroxide, in a solvent mixture of water and methanol or ethanol at a temperature of from 10° to 25° C. The free acid hereby obtained may be converted to a salt with a suitable base.

Step H is a step for forming a mevalonolactone by the dehydration reaction of the free hydroxy acid I-2. The dehydration reaction can be conducted in benzene or toluene under reflux while removing the resulting water or by adding a suitable dehydrating agent such as molecular sieve.

Further, the dehydration reaction may be conducted in dry methylene chloride by using a lactone-forming agent such as carbodiimide, preferably a water soluble carbodiimide such as N-cyclohexyl-N'-[2'-(methylmorpholinium)ethyl]carbodiimide p-toluene sulfonate at a temperature of from 10° to 35° C., preferably from 20° to 25° C.

Step J represents a reaction for hydrogenating the double bond connecting the mevalonolactone moiety and the quinoline ring. This hydrogenation reaction can be conducted by using a catalytic amount of palladium-carbon or rhodium-carbon in a solvent such as methanol, ethanol, tetrahydrofuran or acetonitrile at a temperature of from 0° to 50° C., preferably from 10° to 25° C.

Step K represents a reaction for the synthesis of an $\alpha,\beta$-unsaturated carboxylic acid ester, whereby a trans-form $\alpha,\beta$-unsaturated carboxylic acid ester can be obtained by a so-called Horner-Wittig reaction by using an alkoxycarbonylmethyl phosphonate. The reaction is conducted by using sodium hydride or potassium t-butoxide as the base in dry tetrahydrofuran at a temperature of from −30° to 0° C., preferably from −20° to −15° C.

Step L represents a reduction reaction of the $\alpha,\beta$-unsaturated carboxylic acid ester to an allyl alcohol. This reduction reaction can be conducted by using various metal hydrides, preferably diisobutylaluminiumhydride, in a solvent such as dry tetrahydrofuran or toluene at a temperature of from −10° to 10° C., preferably from −10° to 0° C.

Step M represents an oxidation reaction of the allyl alcohol to an enal. This oxidation reaction can be conducted by using various oxidizing agents, particularly active manganese dioxide, in a solvent such as tetrahydrofuran, acetone, ethyl ether or ethyl acetate at a temperature of from 0° to 100° C., preferably from 15° to 50° C.

Step N represents a reaction for the synthesis of an $\alpha,\beta$-unsaturated ketone by the selective oxidation of the dihydroxy carboxylic acid ester. This reaction can be conducted by using activated manganese dioxide in a solvent such as ethyl ether, tetrahydrofuran, benzene or toluene at a temperature of from 20° to 80° C., preferably from 40° to 80° C.

In addition to the compounds disclosed in Examples given hereinafter, compounds of the formulas I-2 and I-5 given in Table 1 can be prepared by the process of the present invention. In Table 1, i- means iso, sec- means secondary and c- means cyclo. Likewise, Me means methyl, Et means ethyl, Pr means propyl, bu means butyl, Pent means pentyl, Hex means hexyl and Ph means phenyl.

TABLE 1

[Structure: I-2 ($R^{12}$ = H); I-5 ($R^{12}$ = Na)]

| $R^1$ | $R^2$ | $R^3$ | $R^4$ | $R^5$ | $R^6$ |
|---|---|---|---|---|---|
| 6-OMe | H | H | H | i-Pr | H |
| 6-OMe | H | 4-F | H | i-Pr | H |
| 6-Br | H | 4-F | H | i-Pr | H |
| 6-Me | 8-Me | 4-F | H | i-Pr | H |
| 7-OMe | 8-OMe | 4-F | H | i-Pr | H |
| 6-Br | H | 2-F | H | i-Pr | H |
| 6,7-benzo | | 4-F | H | i-Pr | H |
| H | H | 4-F | H | c-Hex | H |
| H | H | 4-Ph | H | i-Pr | H |
| H | H | 4-PhCH$_2$ | H | i-Pr | H |
| 6-Cl | H | 4-F | H | c-Pr | H |
| 6-Cl | H | 4-F | H | sec-Bu | H |
| 6-OCH$_2$Ph | H | 4-F | H | i-Pr | H |
| H | H | 4-F | H | i-Bu | H |
| H | H | 4-F | H | c-Pent | H |
| 6-Cl | H | 4-F | H | c-Pent | H |
| 6-Me$_2$N | H | 4-F | H | i-Pr | H |
| 6-Me | H | 4-F | H | c-Pr | H |
| 6-i-Pr | H | 4-F | H | i-Pr | H |
| 7-Me | H | 4-F | H | c-Pr | H |
| 6-OMe | H | 4-F | H | c-Pr | H |
| 6-Br | H | 4-F | H | c-Pr | H |
| 6-i-Pr | H | 4-F | H | c-Pr | H |
| 6-Cl | 8-Cl | 4-F | H | c-Pr | H |
| 5-F | 6-Br | 4-F | H | i-Pr | 8-Br |
| 6-OMe | 7-OMe | 4-F | H | i-Pr | 8-OMe |
| 6-Me | 7-Me | 4-F | H | i-Pr | 8-Me |
| 6-Cl | 7-Cl | 4-F | H | i-Pr | 8-Cl |
| H | H | 4-F | H | c-Bu | H |
| H | H | 4-F | H | c-Hex | H |
| 6-OMe | 7-OMe | H | H | i-Pr | H |
| 6-OMe | 7-OMe | 4-Cl | H | i-Pr | H |
| 6-OMe | 7-OMe | H | H | c-Pr | H |
| 6-OMe | 7-OMe | 4-Cl | H | c-Pr | H |
| 6-OMe | 7-OMe | 4-F | H | c-Pr | H |
| 6-Me | H | H | H | i-Pr | H |
| 6-Me | H | 4-Cl | H | i-Pr | H |
| 6-Me | H | H | H | c-Pr | H |
| 6-Me | H | 4-Cl | H | c-Pr | H |
| 6-Me | H | 4-F | H | c-Pr | H |
| 6-Cl | H | H | H | i-Pr | H |
| 6-Cl | H | 4-Cl | H | i-Pr | H |
| 6-Cl | H | H | H | c-Pr | H |
| 6-Cl | H | 4-Cl | H | c-Pr | H |
| 6-Cl | H | 4-F | H | c-Pr | H |
| H | H | H | H | i-Pr | H |
| H | H | 4-Cl | H | i-Pr | H |
| H | H | H | H | c-Pr | H |
| H | H | 4-Cl | H | c-Pr | H |
| H | H | 4-F | H | c-Pr | H |

Further, pharmaceutically acceptable salts such as potassium salts or esters such as ethyl esters or methyl esters of these compounds can be prepared in the same manner.

The compounds of the present invention exhibit high inhibitory activities against the cholesterol biosynthesis wherein HMG-CoA reductase acts as a rate limiting enzyme, as shown by the test results given hereinafter, and thus are capable of suppressing or reducing the amount of cholesterol in blood as lipoprotein. Thus, the compounds of the present invention are useful as curing agents against hyperlipidemia, hyperlipoproteinemia and atheroscleosis.

They may be formulated into various suitable formulations depending upon the manner of the administration. The compounds of the present invention may be administered in the form of free acids or in the form of physiologically hydrolyzable and acceptable esters or lactones, or pharmaceutically acceptable salts.

The pharmaceutical composition of the present invention is preferably administered orally in the form of the compound of the present invention per se or in the form of powders, granules, tablets or capsules formulated by mixing the compound of the present invention with a suitable pharmaceutically acceptable carrier including a binder such as hydroxypropyl cellulose, syrup, gum arabic, gelatin, sorbitol, tragacanth gum, polyvinyl pyrrolidone or CMC-Ca, an excipient such as lactose, sugar, corn starch, calcium phosphate, sorbitol, glycine or crystal cellulose powder, a lubricant such as magnesium stearate, talk, polyethylene glycol or silica, and a disintegrator such as potato starch.

However, the pharmaceutical composition of the present invention is not limited to such oral administration and it is applicable for parenteral administration. For example, it may be administered in the form of e.g. a suppository formulated by using oily base material such as cacao butter, polyethylene glycol, lanolin or fatty acid triglyceride, a transdermal therapeutic base formulated by using liquid paraffin, white vaseline, a higher alcohol, Macrogol ointment, hydrophilic ointment or hydro-gel base material, an injection formulation formulated by using one or more materials selected from the group consisting of polyethylene glycol, hydro-gel base material, distilled water, distilled water for injection and excipient such as lactose or corn starch, or a formulation for administration through mucous membranes such as an ocular mucous membrane, a nasal mucous membrane and an oral mucous membrane.

Further, the compounds of the present invention may be combined with basic ion-exchange resins which are capable of binding bile acids and yet not being absorbed in gastraintestinal tract.

The daily dose of the compound of the formula I is from 0.05 to 500 mg, preferably from 0.5 to 50 mg for an adult. It is administered from once to three times per day. The dose may of course be varied depending upon the age, the weight or the condition of illness of the patient.

The compounds of the formulas II to VII are novel, and they are important intermediates for the preparation of the compounds of the formula I. Accordingly, the present invention relates also to the compounds of the formulas II to VII and the processes for their production.

Now, the present invention will be described in further detail with reference to Test Examples for the pharmacological activities of the compounds of the present invention, their Preparation Examples and Formulation Examples. However, it should be understood that the present invention is by no means restricted by such specific Examples.

PHARMACOLOGICAL TEST EXAMPLES

Test A:

Inhibition of Cholesterol Biosynthesis from Acetate In Vitro

Enzyme solution was prepared from liver of male Wistar rat billialy cannulated and discharged bile for over 24 hours. Liver was cut out at mid-dark and microsome and supernatant fraction which was precipitable with 40-80% of saturation of ammonium sulfate (sup fraction) were prepared from liver homogenate according to the modified method of Knauss et. al.; Kuroda, M., et. al., Biochim. Biophys. Acta, 489, 119 (1977). For assay of cholesterol biosynthesis, microsome (0.1 mg protein) and sup fraction (1.0 mg protein) were incubated for 2 hours at 37° C. in 200 µl of the reaction mixture containing ATP; 1 mM, Glutathione; 6 mM, Glucose-1-phosphate; 10 mM, NAD; 0.25 mM, NADP; 0.25 mM, CoA; 0.04 mM and 0.2 mM [2-$^{14}$C]sodium acetate (0.2 µCi) with 4 µl of test compound solution dissolved in water or dimethyl sulfoxide. To stop reaction and saponify, 1 ml of 15% EtOH—KOH was added to the reactions and heated at 75° C. for 1 hour. Nonsaponifiable lipids were extracted with petroleum ether and incorporated $^{14}$C radioactivity was counted. Inhibitory activity of compounds was indicated with IC50.

Test B:

Inhibition of Cholesterol Biosynthesis in Culture Cells

Hep G2 cells at over 5th passage were seeded to 12 well plates and incubated with Dulbecco's modified Eagle (DME) medium containing 10% of fetal bovine serum (FBS) at 37° C., 5% $CO_2$ until cells were confluent for about 7 days. Cells were exposed to the DME medium containing 5% of lipoprotein deficient serum (LpDS) prepared by ultracentrifugation method for over 24 hours. Medium was changed to 0.5 ml of fresh 5% LpDS containing DME before assay and 10 µl of test compound solution dissolved in water or DMSO were added. 0.2 µCi of [2-$^{14}$C]sodium acetate (20 µl) was added at 0 hr(B-1) or 4 hrs(B-2) after addition of compounds. After 4 hrs further incubation with [2-$^{14}$C]sodium acetate, medium was removed and cells were washed with phosphate buffered saline(PBS) chilled at 4° C. Cells were scraped with rubber policeman and collected to tubes with PBS and digested with 0.2 ml of 0.5N KOH at 37° C. Aliquot of digestion was used for protein analysis and remaining was saponified with 1 ml of 15% EtOH-KOH at 75° C. for 1 hour. Nonsaponifiable lipids were extracted with petroleum ether and $^{14}$C radioactivity was counted. Counts were revised by cell protein and indicated with DPM/mg protein. Inhibitory activity of compounds was indicated with IC50.

Test C:

Inhibition of Cholesterol Biosynthesis in vivo

Male Sprague-Dawley rats weighing about 150 g were fed normal Purina chow diet and water ad libitum, and exposed to 12 hours light/12 hours dark lighting pattern (2:00 PM-2:00 AM dark) prior to use for in vivo inhibition test of cholesterol biosynthesis. Animals were separated groups consisting of five rats as to be average mean body weight in each groups. Test compounds at dosage of 0.02-0.2 mg/kg body weight (0.4 ml/100 g body weight), were dissolved in water or suspended or in 0.5% methyl cellulose and orally administered at 2-3 hours before mid-dark (8:00 PM), while cholesterol biosynthesis reaches to maximum in rats. As control, rats were orally administered only water or vehicle. At 90 minutes after sample administration, rats were injected intraperitoneally with 10 µCi of [2-$^{14}$C]sodium acetate at volume of 0.2 ml per one. 2 Hours later, blood samples were obtained and serum were separated immediately. Total lipids were extracted according to the method of Folch et al. and saponified with EtOH-KOH. Nonsaponifiable lipids were extracted with petroleum ether and radio activity incorporated into nonsaponifiable lipids was counted.

Inhibitory activity was indicated as percent decrease of counts in testing groups (DPM/2 ml serum/2 hours) from that in control group.

With respect to the compounds of the present invention, the inhibitory activities against the cholesterol biosynthesis in which HMG-CoA reductase serves as a rate limiting enzyme, were measured by the above Test A and B. The results are shown in Tables, 2, 2-2, 3 and 3-2. Further, the results of the measurements by Test C are also presented.

TABLE 2

| Inhibitory activities by Test A | |
|---|---|
| Compound | $I_{50}$ (molar concentration) |
| (Compounds of the present invention) | |
| I-13 | $1.25 \times 10^{-7}$ |
| I-51 | $1.0 \times 10^{-8}$ |
| I-52 | $7.1 \times 10^{-8}$ |
| I-53 | $1.9 \times 10^{-7}$ |
| (Reference compounds) | |
| Mevinolin | $1.4 \times 10^{-8}$ |
| CS-514 | $9.0 \times 10^{-9}$ |

In Table 2-2, the relative activities are shown based on the activities of CS-514 being evaluated to be 1.

TABLE 2-2

| Relative activities by Test A | |
|---|---|
| Compound | Relative activities |
| (Compounds of the present invention) | |
| I-16 | 1.75 |
| I-116 | 2.25 |
| I-117 | 0.37 |
| I-120 | 3.21 |
| I-522 | 0.76 |

Structures of reference compounds:
(1) Mevinolin

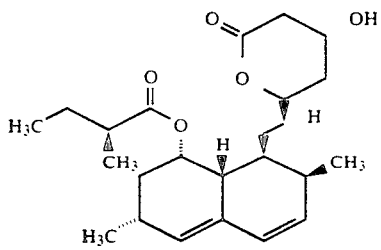

(2) CS-514

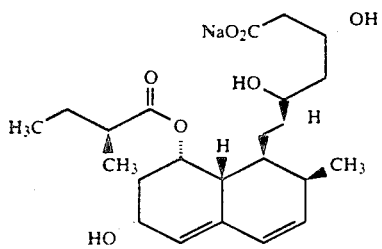

TABLE 3

| Inhibitory activities by Test B-1 | |
|---|---|
| Compound | I₅₀ (molar concentration) |
| (Compound of the present invention) | |
| I-51 | 1 × 10⁻⁷ |
| (Reference compound) | |
| CS-514 | 3.5 × 10⁻⁷ |

In Table 3-2, the relative activities are shown based on the activities of CS-514 being evaluated to be 1.

TABLE 3-2

| Relative activities by Test B-1 | |
|---|---|
| Compound | Relative activities |
| I-116 | 19.4 |
| I-520 | 20.0 |
| II-20 | 20.8 |

Results of the Measurement of the Inhibitory Activities by Test C

The percent decrease of counts after the oral administration of 0.05 mg/kg of compound I-520 was 55% relative to the measured value of the control group. The percent decrease of counts after the oral administration of 10 mg/kg of CS-514 was 55% under the same condition. The compounds of the present invention exhibited activities superior to the reference compound such as CS-514 or Mevinolin in Test A, and exhibited activities superior to CS-514 in Tests B and C.

Test D

Acute Toxicity

A 0.5% CMC suspension of a test compound was orally administered to ICR male mice (group of three mice). The acute toxicity was determined based on the mortality after seven days. With compound I-57, I-58, I-59, I-511, I-512, I-513, I-514, I-515, I-517 and I-523 of the present invention, the mortality was 0% even when they were orally administered in an amount of 1000 mg/kg.

EXAMPLE 1

Ethyl (E)-3,5-dihydroxy-7-[4'-(4"-fluorophenyl)-2'-(1"-methylethyl)-quinolin-3'-yl]-hept-6-enoate (compound I-11) (prepared by steps of Example 1-a through Example 1-q)

EXAMPLE 1-a

Ethyl 4-(4'-fluorophenyl)-2-(1'-methylethyl)-quinolin-3-yl-carboxylate (compound VII-1)

The synthesis was conducted in accordance with the method disclosed in J. Org. Chem., 2899 (1966).

6.45 g (0.03 mol) of 2-amino-4'-fluorobenzophenone, 5.53 g (0.035 mol) of ethyl isobutyrylacetate and 0.1 ml of conc. sulfuric acid were dissolved in 30 ml of glacial acetic acid, and the mixture was heated at 100° C. for about 10 hours. After confirming the substantial disappearance of 2-amino-4'-fluorobenzophenone by thin layer chromatography, the reaction solution was cooled to room temperature, and a mixture of 45 ml of conc. aqueous ammonia and 120 ml of water cooled with ice, was gradually added thereto. A separated oily substance was solidified when left to stand overnight in a refrigerator. This solid was recrystallized from a small amount of ethanol to obtain 6.47 g (55%) of white powder. Melting point: 68°–70.5° C.

EXAMPLE 1-b:

4-(4'-fluorophenyl)-3-hydroxymethyl-2-(1'-methylethyl)-quinoline (compound VI-1)

5.4 g (0.016 mol) of compound VII-1 was dissolved in dry toluene under a nitrogen atmosphere and cooled in ice bath to 0° C. To this solution, 40 ml of a 16 wt % diisobutylaluminium hydride-toluene solution was dropwise added, and the mixture was stirred at 0° C. for two hours. After confirming the complete disappearance of compound VII-1 by thin layer chromatography, a saturated ammonium chloride solution was added thereto at 0° C. to terminate the reaction. Ethyl ether was added to the reaction mixture, and the organic layer was separated. A gelled product was dissolved by an addition of an aqueous sodium hydroxide solution and extracted anew with ethyl ether. The ethyl ether extracts were put together, dried over anhydrous magnesium sulfate and filtered. The solvent was distilled off. The residual oil underwent crystallization when left to stand. It was recrystallized from ethyl acetate-n-hexane to obtain 3.3 g of white crystals. Yield: 70%. Melting point: 136°–137° C.

EXAMPLE 1-c:

4-(4'-fluorophenyl)-2-(1'-methylethyl)-quinolin-3-yl-carboxyaldehyde (compound V-1)

2.0 g (9.3 mmol) of pyridinium chlorochromate and 0.4 g of anhydrous sodium acetate was suspended in 10 ml of dry dichloromethane. To this suspension, a solution obtained by dissolving 1 g (3.4 mmol) of compound VI-1 in 10 ml of dry dichloromethane, was immediately added at room temperature. The mixture was stirred for one hour. Then, 100 ml of ethyl ether was added thereto, and the mixture was throughly mixed. The reaction mixture was filtered under suction through a silica gel layer. The filtrate was dried under reduced pressure. The residue was dissolved in the isopropyl ether, and insoluble substances were filtered off. The filtrate was again dried under reduced pressure, and the residue was recrystallized from diisopropyl ether to obtain 0.7 g (Yield: 70%) of slightly yellow prism crystals. Melting point: 124°–126° C.

EXAMPLE 1-d:

3-(3'-ethoxy-1'-hydroxy-2'-propenyl)-4-(4'-fluorophenyl)-2-(1'-methylethyl)-quinoline (compound IV-1)

1.13 g (3.13 mmol) of cis-1-ethoxy-2-(tri-n-butylstannyl)ethylene was dissolved in 8 ml of dry tetrahydrofuran, and the solution was cooled to −78° C. in a nitrogen stream. To this solution, 2 ml (3.2 mmol) of a 15 wt % n-butyllithium-n-hexane solution was dropwise added. The mixture was stirred for 45 minutes. Then, a solution prepared by dissolving 0.76 g (2.6 mmol) of compound V-1 in 10 ml of dry tetrahydrofuran was dropwise added thereto. The reaction mixture was stirred at −78° C. for two hours. Then, 2 ml of a saturated ammonium chloride solution was added thereto to terminate the reaction. The organic layer was extracted with diethyl ether, and the diethyl ether extract was washed with a saturated sodium chloride aqueous solution and dried over anhydrous magnesium sulfate. The solvent was distilled off under reduced pressure. The residue was separated with n-hexane and acetonitrile. The solvent was distilled off under reduced pressure from the acetonitrile layer, and an oily substance thereby obtained was purified by silica gel column chromatography (eluent: 2.5% methanol-chloroform) to obtain 0.91 g of the desired compound in a purified oily form.

H—MNR (CDCl$_3$) δ ppm: 1.1(t,3H,7 Hz), 1.37(d,6H,J=7 Hz), 3.7(m,1H) 3.7(q,2H,J=7 Hz), 4.75(t,1H,7 Hz), 5.7(m,1H), 5.95(m,1H), 7.05–8.2(m,8H),

EXAMPLE 1-e:

(E)-3-[4'-(4''-fluorophenyl)-2'-(1''-methylethyl)-quinolin-3'-yl]propenaldehyde (compound III-1)

0.91 g of compound IV-1 was dissolved in 20 ml of tetrahydrofuran, and 5 ml of water and 100 mg of p-toluenesulfonic acid were added thereto. The mixture was stirred at room temperature for 24 hours. The reaction solution was extracted with diethyl ether a few times. The extracts were washed with a saturated sodium chloride aqueous solution and dried over anhydrous magnesium sulfate. Then, the solvent was distilled off. The residue was purified by silica gel column chromatography (eluent: chloroform) to obtain the desired product as white prism crystals. 0.4 g (50%). Melting point: 127°–128° C.

EXAMPLE 1-f: Ethyl (E)-7-[4'-(4''-fluorophenyl)-2'-(1''-methylethyl)-quinolin-3'-yl]-5-hydroxy-3-oxohepto-6-enoate (compound II-1)

50 mg of 60% sodium hydride was washed with dry petroleum ether and dried under a nitrogen stream, and then suspended in 5 ml of dry tetrahydrofuran. The suspension was cooled to −15° C. in a nitrogen atmosphere. Then, 120 mg (0.92 mmol) of ethyl acetoacetate was dropwise added thereto, and the mixture was stirred for 15 minutes. Then, 0.6 ml (0.92 mmol) of a 15 wt % n-butyllithium-n-hexane solution was dropwise added thereto, and the mixture was stirred for 30 minutes. Then, a solution prepared by dissolving 160 mg (0.5 mmol) of compound III-1 in dry tetrahydrofuran, was dropwise added thereto, and the mixture was stirred for one hour. To the reaction mixture, 1 ml of a saturated ammonium chloride aqueous solution was added at −15° C. Then, the mixture was extracted three times with diethyl ether. The diethyl ether solution was washed with a saturated sodium chloride aqueous solution and dried over anhydrous magnesium sulfate. The solution was evaporated to dryness under reduced pressure. The residue was recrystallized from diisopropyl ether to obtain 130 mg (yield: 59%) of white crystals. Melting point: 99°–101° C.

EXAMPLE 1-g: Ethyl (E)-3,5-dihydroxy-7-[4'-(4''-fluorophenyl)-2'-(1''-methylethyl)-quinolin-3'-yl]-hept-6-enoate (compound I-11)

110 mg (0.245 mmol) of compound II-1 was dissolved in 5 ml of ethanol in a nitrogen atmosphere, and the solution was cooled 0° C. Then, 10 mg (0.263 mmol) of sodium borohydride was added, and the mixturer was stirred for one hour. Then, 1 ml of a 10% hydrochloric acid aqueous solution was added thereto, and the mixture was extracted three times with ethyl ether. The ethyl ether solution was washed with a saturated sodium chloride aqueous solution and dried over anhydrous magnesium sulfate. Then, the solution was evaporated to dryness under reduced pressure. The residual oil was purified by silica gel column chromatography (eluent: 5% methanol-chloroform) to obtain the desired product as a pure colorless oily substance. 70 mg (Yield: 64%).

H—NMR (CDCl$_3$) δ ppm: 1.30(t, 3H, J=8 Hz), 1.39(d, 6H, J=8 Hz), 1.4–1.8(m, 2H), 2.42(d, 2H, J=7 Hz), 3.0–3.8 (m, 2H), 3.50(m, 1H), 3.9–4.6(m, 2H), 4.20(q, 2H, J=8 Hz), 5.35(m, 1H), 6.59(m, 1H), 7.10–8.18(m, 8H).

EXAMPLE 2

Sodium salt of (E)-3,5-dihydroxy-7-[4'-(4''-fluorophenyl)-2'-(1''-methylethyl)-quinolin-3'-yl]-hept-6-enoic acid (compound I-51)

60 mg (0.133 mmol) of compound I-11 was dissolved in 3 ml of ethanol. Then, 0.26 ml of a 0.5N sodium hydroxide aqueous solution was dropwise added thereto. The mixture was stirred at room temperature for further one hour, and ethanol was distilled off under reduced pressure. Then, 5 ml of water was added thereto, and the mixture was extracted with ethyl ether. The aqueous layer was freeze-dried to obtain 40 mg (67%) of hygroscopic white powder. Melting point: 207°–209° C. (decomposed).

EXAMPLE 3

(E)-3,5-dihydroxy-7-[4'-(4''-fluorophenyl)-2'-(1''-methylethyl)-quinolin-3'-yl]-hept-6-enoic acid (compound I-21)

110 mg (0.244 mmol) of compound I-11 was dissolved in 10 ml of ethanol. Then, 0.79 ml of a 0.5N sodium hydroxide aqueous solution was dropwise added thereto. The mixture was stirred at room temperature for further one hour, and ethanol was distilled off under reduced pressure. Then, 10 ml of water was added thereto, and the mixture was extracted with ethyl ether. The aqueous layer was weakly acidified (pH 4) with a dilute hydrochloric aqueous solution and extracted three times with ethyl ether. The ethyl ether layers were put together and dried over anhydrous magnesium sulfate. Then, the solvent was distilled off under reduced pressure to obtain 90 mg of slightly yellow oily substance.

H—NMR (CDCl$_3$) δ ppm: 1.36(d, 6H, J=7 Hz), 2.4(m, 2H), 3.5(m, 1H), 3.45(m, 1H), 3.8–4.6(m, 2H), 5.40(dd, 1H, J$_1$=19 Hz, J$_2$=8 Hz), 6.55 (d, 1H, J=19 Hz), 7.0–8.3(m, 8H).

EXAMPLE 4

(E)-6-[4'-(4''-fluorophenyl)-2'-(1''-methylethyl)-quinolin-3'-ylethenyl]-4-hydroxy-3,4,5,6-tetrahydro-2H-pyran-2-one (compound I-31)

90 mg of compound I-21 was dissolved in 10 ml of dry toluene, and the solution was refluxed under heating for 3 hours by means of a Dean Stark apparatus.

Toluene was distilled off under reduced pressure, and the residual solid was recrystallized from diisopropyl ether to obtain 40 mg of colorless prism crystals. Melting point: 182°–184° C.

By silica gel thin chromatography, the product gave two absorption spots close to each other attributable to the diastereomers. (Developing solvent: 3% methanol-chloroform)

These diasteromers were separated and isolated by silica gel thin layer chromatography. [Developing solvent: t-BuOMe/hexane/acetone=7/2/1 (v/v), Rf=0.6 and 0.7 (obtained weight ratio: ½)].

Rf=0.7: trans lactone

H—NMR (CDCl$_3$) δ ppm: 1.40(d, 6H, J=7 Hz), 1.6(m, 2H), 2.65(m, 2H), 3.48(m, 1H), 4.20(m, 1H), 5.15(m, 1H), 5.37(dd, 1H, J$_1$=18 Hz, J$_2$=7 Hz), 6.68(d, 1H, J=19 Hz), 7.1–8.2(m, 8H).

Rf=0.6: cis lactone

H—NMR (CDCl$_3$) δ ppm: 1.40(d, 6H, J=7 Hz), 1.6(m, 2H), 2.65(m, 2H), 3.48(m, 1H), 4.20(m, 1H), 4.65(m, 1H), 5.40(dd, 1H, J$_1$=18 Hz, J$_2$=7 Hz), 6.66(m, 1H), 7.0–8.2(m, 8H).

EXAMPLE 5

6-[4'-(4''-fluorophenyl)-2'-(1''-methylethyl)-quinolin-3'-ylethynyl]-4-hydroxy-3,4,5,6-tetrahydro-2H-pyran-2-one (compound I-41)

20 mg of a mixture of diastereomers of compound I-31 was dissolved in 5 ml of ethanol, and 10 mg of 5% palladium-carbon was added thereto. The mixture was stirred under a hydrogen atmosphere. After confirming the disappearance of the starting substance and the appearance of a new spot by thin layer chromatography, the palladium-carbon was filtered off, and ethanol was distilled off to obtain colorless oil.

This oil was purified by preparative thin layer chromatography to obtain 16 mg of the desired product as pure colorless oil.

MS(m/e): 408(M$^+$+H), 407(M$^+$), 366, 292, 278.

In the same manner as in Example 1-a, compounds VII-2 to VII-27 were prepared. The physical properties of these compounds are shown in Table 4. (In the Table, R$^1$, R$^2$, R$^3$, R$^4$, R$^5$ and R$^{21}$ correspond to the substitients of compound VII.)

TABLE 4

| (Compounds in this Table are compounds of the formula VII wherein R$^6$ is hydrogen.) | | | | | | |
|---|---|---|---|---|---|---|
| Compound | R$^1$ | R$^2$ | R$^3$ | R$^4$ | R$^5$ | R$^{21}$ | m. p. (°C.) |
| VII-2 | H | H | 4-F | H | CH$_3$ | C$_2$H$_5$ | 121–122 |
| VII-3 | H | H | H | H | CH$_3$ | C$_2$H$_5$ | 102–102.5 |
| VII-4 | H | H | H | H | i-Pr | C$_2$H$_5$ | 85–85.5 |
| VII-5 | 6-Cl | H | H | H | CH$_3$ | C$_2$H$_5$ | 100.5–101.5 |
| VII-6 | 6-Cl | H | H | H | i-Pr | C$_2$H$_5$ | 105.5–106.5 |
| VII-7 | H | H | 2-F | H | i-Pr | C$_2$H$_5$ | 101.0–102.0 |
| VII-8 | 7-Me | H | H | H | i-Pr | C$_2$H$_5$ | oil |
| VII-9 | H | H | 4-Cl | H | i-Pr | C$_2$H$_5$ | 134.0–136.5 |
| VII-10 | H | H | 4-OMe | H | i-Pr | C$_2$H$_5$ | 88.0–89.0 |
| VII-11 | H | H | 4-Me | H | i-Pr | C$_2$H$_5$ | 108.5–109.5 |
| VII-12 | 6-Cl | H | 2-Cl | H | i-Pr | C$_2$H$_5$ | 101.0–103.0 |
| VII-13 | H | H | 4-CF$_3$ | H | i-Pr | C$_2$H$_5$ | 117.5–119.0 |
| VII-14 | H | H | 3-Me | 4-F | i-Pr | C$_2$H$_5$ | oil |
| VII-15 | H | H | 3-Me | 5-Me | i-Pr | C$_2$H$_5$ | oil |
| VII-16 | 6-OMe | 7-OMe | 4-F | H | i-Pr | C$_2$H$_5$ | 96.0–98.0 |
| VII-17 | H | H | 4-F | H | C$_2$H$_5$ | CH$_3$ | 139.0–139.5 |
| VII-18 | H | H | 4-F | H | n-Pr | C$_2$H$_5$ | oil |
| VII-19 | 6-Cl | H | 4-F | H | i-Pr | C$_2$H$_5$ | 94.5–95.5 |
| VII-20 | H | H | 4-F | H | c-Pr | CH$_3$ | 113.5–116.5 |
| VII-21 | H | H | 4-OPh | H | i-Pr | C$_2$H$_5$ | oil |
| VII-22 | 6-Cl | 8-Cl | 4-F | H | i-Pr | C$_2$H$_5$ | 96.0–98.0 |
| VII-23 | 6-Cl | H | H | H | Ph | C$_2$H$_5$ | 118.8–119.5 |
| VII-24 | 6-Cl | H | H | H | c-Pr | CH$_3$ | 97.0–98.5 |
| VII-25 | H | H | 4-F | H | sec-Bu | CH$_3$ | oil |
| VII-26 | 6-Me | H | 4-F | H | i-Pr | C$_2$H$_5$ | 109.0–111.0 |
| VII-27 | 6-OMe | 7-OMe | 4-F | H | c-Pr | CH$_3$ | 153.0–153.5 |

VII-8

H—NMR (in CDCl$_3$) δ ppm: 0.92 (t, 3H, J=7 Hz), 1.41 (d, 6H, J=6 Hz), 2.47 (s, 3H), 3.27(Heptaplet, 1H, J=6 Hz), 3.96 (q, 2H, J=7 Hz), 7.0–7.8(m, 8H).

VII-14

H—NMR (in CDCl$_3$) δ ppm: 1.01 (t, 3H, J=7 Hz), 1.42 (d, 6H, J=6 Hz), 2.38 (s, 3H, J=3 Hz), 3.25(Heptaplet, 1H, J=6 Hz), 4.04 (q, 2H, J=7 Hz), 6.9–8.1(m, 7 Hz).

VII-15

H—NMR (in CDCl$_3$) δ ppm: 0.97 (t, 3H, J=7 Hz), 1.43 (d, 6H, J=6 Hz), 2.29 (s, 6H), 3.25(Heptaplet, 1H, J=6 Hz), 4.00 (q, 2H, J=7 Hz), 6.8–8.0(m, 7H).

VII-18

H—NMR (in CDCl$_3$) δ ppm: 0.98 (t, 3H, J=7 Hz), 1.02 (t, 3H, J=7 Hz), 1.6–2.3(m, 2H), 2.8–3.1(m, 2H), 4.03 (q, 2H, J=7 Hz), 6.9–8.1(m, 8H).

VII-21

H—NMR (in CDCl$_3$) δ ppm: 1.03 (t, 3H, J=7 Hz), 1.41 (d, 6H, J=6 Hz), 3.25(Heptaplet, 1H, J=6 Hz), 4.05(q, 2H, J=7 Hz), 6.8-8.1(m, 13H).

VII-25

H-NMR (in CDCl$_3$) δ ppm: 0.97 (d, 6H, J=6 Hz), 2.0~2.6(m, 1H), 2.85 (d, 2H, J=7 Hz), 3.51(s, 3H), 6.8-8.1(m, 8H).

In the same manner as in Example 1-b, compounds VI-2 to VI-27 were prepared. (In Table 5, R$^1$, R$^2$, R$^3$, R$^4$ and R$^5$ correspond to the substituents in compound VI.)

TABLE 5

(Compounds in this Table are compounds of the formula VI wherein R$^6$ is hydrogen.)

| Compound | R$^1$ | R$^2$ | R$^3$ | R$^4$ | R$^5$ | m. p. (°C.) |
|---|---|---|---|---|---|---|
| VI-2 | H | H | p-F | H | CH$_3$ | — |
| VI-3 | H | H | H | H | CH$_3$ | 149-151 |
| VI-4 | H | H | H | H | i-Pr | 130-130.5 |
| VI-5 | 6-Cl | H | H | H | CH$_3$ | 139-141 |
| VI-6 | 6-Cl | H | H | H | i-Pr | 168-169 |
| VI-7 | H | H | 2-F | H | i-Pr | 140.5-142.0 |
| VI-8 | 7-Me | H | H | H | i-Pr | 155.0-157.0 |
| VI-9 | H | H | 4-Cl | H | i-Pr | 192.0-195.0 |
| VI-10 | H | H | 4-OMe | H | i-Pr | 186.0-188.5 |
| VI-11 | H | H | 4-Me | H | i-Pr | 161.0-164.0 |
| VI-12 | 6-Cl | H | 2-Cl | H | i-Pr | 122.0-124.0 |
| VI-13 | H | H | 4-CF$_3$ | H | i-Pr | 183.0-186.0 |
| VI-14 | H | H | 3-Me | 4-F | i-Pr | 161.0-162.5 |
| VI-15 | H | H | 3-Me | 5-Me | i-Pr | 137.0-138.0 |
| VI-16 | 6-Me | 7-OMe | 4-F | H | i-Pr | 164.0-165.0 |
| VI-17 | H | H | 4-F | H | C$_2$H$_5$ | 141.5-143.5 |
| VI-18 | H | H | 4-F | H | n-Pr | 146.5-148.5 |
| VI-19 | 6-Cl | H | 4-F | H | i-Pr | 171.0-172.0 |
| VI-20 | H | H | 4-F | H | c-Pr | 120-126 |
| VI-21 | H | H | 4-OPh | H | i-Pr | 153.0-154.0 |
| VI-22 | 6-Cl | 8-Cl | 4-F | H | i-Pr | 98.5-103 |
| VI-23 | 6-Cl | H | H | H | Ph | 171.5-172.5 |
| VI-24 | 6-Cl | H | H | H | c-Pr | 84.0-86.0 |
| VI-25 | H | H | 4-F | H | sec-Bu | 119.0-121.0 |
| VI-26 | 6-Me | H | 4-F | H | i-Pr | 160.0-161.5 |
| VI-27 | 6-OMe | 7-OMe | 4-F | H | c-Pr | 162.0-163.0 |

In the same manner as in Example 1-c, compounds V-2 to V-27 were prepared. (In Table 6, R$^1$, R$^2$, R$^3$, R$^4$ and R$^5$ correspond to the substituents of compound V.)

TABLE 6

(Compounds in this Table are compounds of the formula V wherein R$^6$ is hydrogen.)

| Compound | R$^1$ | R$^2$ | R$^3$ | R$^4$ | R$^5$ | m. p. (°C.) |
|---|---|---|---|---|---|---|
| V-2 | H | H | p-F | H | CH$_3$ | 125-128 |
| V-3 | H | H | H | H | CH$_3$ | 143-146 |
| V-4 | H | H | H | H | i-Pr | 92-93 |
| V-5 | 6-Cl | H | H | H | CH$_3$ | 220-222 |
| V-6 | 6-Cl | H | H | H | i-Pr | 140-140.5 |
| V-7 | H | H | 2-F | H | i-Pr | 121.5-124.0 |
| V-8 | 7-Me | H | H | H | i-Pr | 105.1-109.2 |
| V-9 | H | H | 4-Cl | H | i-Pr | 147.0-147.8 |
| V-10 | H | H | 4-OMe | H | i-Pr | 135.6-136.8 |
| V-11 | H | H | 4-Me | H | i-Pr | 119.4-120.4 |
| V-12 | 6-Cl | H | 2-Cl | H | i-Pr | 105.8-106.9 |
| V-13 | H | H | 4-CF$_3$ | H | i-Pr | 163.7-164.2 |
| V-14 | H | H | 3-Me | 4-F | i-Pr | 161.1-108.1 |
| V-15 | H | H | 3-Me | 5-Me | i-Pr | 120.8-122.3 |
| V-16 | 6-OMe | 7-OMe | 4-F | H | i-Pr | 164.4-165.2 |
| V-17 | H | H | 4-F | H | C$_2$H$_5$ | 143.1-144.2 |
| V-18 | H | H | 4-F | H | n-Pr | 150.2-155.3 |
| V-19 | 6-Cl | H | 4-F | H | i-Pr | 164.5-165.3 |
| V-20 | H | H | 4-F | H | c-Pr | 150.1-151.6 |
| V-21 | H | H | 4-OPh | H | i-Pr | 106.9-107.7 |

TABLE 6-continued (Compounds in this Table are compounds of the formula V wherein R$^6$ is hydrogen.)

| Compound | R$^1$ | R$^2$ | R$^3$ | R$^4$ | R$^5$ | m. p. (°C.) |
|---|---|---|---|---|---|---|
| V-22 | 6-Cl | 8-Cl | 4-F | H | i-Pr | 135.0-135.7 |
| V-23 | 6-Cl | H | H | H | Ph | 174.8-175.3 |
| V-24 | 6-Cl | H | H | H | c-Pr | 157.5-158.0 |
| V-25 | H | H | 4-F | H | sec-Bu | 125.0-126.5 |
| V-26 | 6-Me | H | 4-F | H | i-Pr | 155.0-157.0 |
| V-27 | 6-OMe | 7-OMe | 4-F | H | c-Pr | 200.0-200.5 |

In the same manner as in Example 1-d, compounds IV-2 to IV-6 were prepared. (In Table 7, R$^1$, R$^2$, R$^3$, R$^4$ and R$^5$ correspond to the substituents of compound IV.)

TABLE 7

(Compounds in this Table are compounds of the formula IV wherein R$^6$ is hydrogen.)

| Compound | R$^1$ | R$^2$ | R$^3$ | R$^4$ | R$^5$ | m. p. (°C.) |
|---|---|---|---|---|---|---|
| IV-2 | H | H | 4-F | H | CH$_3$ | 177-179 |
| IV-3 | H | H | H | H | CH$_3$ | — |
| IV-4 | H | H | H | H | i-Pr | — |
| IV-5 | 6-Cl | H | H | H | CH$_3$ | — |
| IV-6 | 6-Cl | H | H | H | i-Pr | — |

In the same manner as in Example 1-e, compounds III-2 to III-27 were prepared. (In Table 8, R$^1$, R$^2$, R$^3$, R$^4$ and R$^5$ correspond to the substituents of compound III.)

TABLE 8

(Compounds in this Table are compounds of the formula III wherein R$^6$ is hydrogen.)

| Compound | R$^1$ | R$^2$ | R$^3$ | R$^4$ | R$^5$ | m. p. (°C.) |
|---|---|---|---|---|---|---|
| III-2 | H | H | 4-F | H | CH$_3$ | 194-196 |
| III-3 | H | H | H | H | CH$_3$ | 170-171.5 |
| III-4 | H | H | H | H | i-Pr | 107-108.5 |
| III-5 | 6-Cl | H | H | H | CH$_3$ | 192-194 |
| III-6 | 6-Cl | H | H | H | i-Pr | 125.5-127 |
| III-7 | H | H | 2-F | H | i-Pr | 80.1-80.2 |
| III-8 | 7-Me | H | H | H | i-Pr | 121.1-122.3 |
| III-9 | H | H | 4-Cl | H | i-Pr | 148.0-149.1 |
| III-10 | H | H | 4-OMe | H | i-Pr | 137.4-140.1 |
| III-11 | H | H | 4-Me | H | i-Pr | 111.6-113.1 |
| III-12 | 6-Cl | H | 2-Cl | H | i-Pr | 83.8-84.5 |
| III-13 | H | H | 4-CF$_3$ | H | i-Pr | 126.2-128.8 |
| III-14 | H | H | 3-Me | 4-F | i-Pr | 124.8-126.4 |
| III-15 | H | H | 3-Me | 5-Me | i-Pr | 117.6-120.3 |
| III-16 | 6-OMe | 7-OMe | 4-F | H | i-Pr | 147.8-150.9 |
| III-17 | H | H | 4-F | H | C$_2$H$_5$ | 124.3-128.5 |
| III-18 | H | H | 4-F | H | n-Pr | 117.8-121.5 |
| III-19 | 6-Cl | H | 4-F | H | i-Pr | 135.2-135.9 |
| III-20 | H | H | 4-F | H | c-Pr | 141.3-144.1 |
| III-21 | H | H | 4-OPh | H | i-Pr | oil |
| III-22 | 6-Cl | 8-Cl | 4-F | H | i-Pr | 117-122 |
| III-23 | 6-Cl | H | H | H | Ph | 142.8-144.3 |
| III-24 | 6-Cl | H | H | H | c-Pr | 161.0-161.5 |
| III-25 | H | H | 4-F | H | sec-Bu | 78.0-81.0 |
| III-26 | 6-Me | H | 4-F | H | i-Pr | 137.0-137.5 |
| III-27 | 6-OMe | 7-OMe | 4-F | H | c-Pr | 189.5-191.0 |

II-2 2

H—NMR (in CDCl$_3$) δ ppm: 1.40(d, 6H, J=7 Hz), 3.44(Heptaplet, 1H, J=7 Hz), 5.93(dd, 1H, J=8 Hz, J=16 Hz), 6.8-8.1(m, 14H), 9.34(d, 1H, J=8 Hz).

In the same manner as in Example 1-f, compounds II-2 to II-27 were prepared. (In Table 9, R$^1$, R$^2$, R$^3$, R$^4$ and R$^5$ correspond to the substituents of compound II.)

TABLE 9

(Compounds in this Table are compounds of the formula of II wherein $R^6$ is hydrogen.)

| Compound | $R^1$ | $R^2$ | $R^3$ | $R^4$ | $R^5$ | $R^{12}$ | m. p. (°C.) |
|---|---|---|---|---|---|---|---|
| II-2 | H | H | p-F | H | $CH_3$ | $C_2H_5$ | oil |
| II-3 | H | H | H | H | $CH_3$ | $C_2H_5$ | 105–106 |
| II-4 | H | H | H | H | i-Pr | $C_2H_5$ | 88.5–90.5 |
| II-5 | 6-Cl | H | H | H | $CH_3$ | $C_2H_5$ | 77–82 |
| II-6 | 6-Cl | H | H | H | i-Pr | $C_2H_5$ | 96–98 |
| II-7 | H | H | 2-F | H | i-Pr | $C_2H_5$ | oil |
| II-8 | 7-Me | H | H | H | i-Pr | $C_2H_5$ | 68.5–74.0 |
| II-9 | H | H | 4-Cl | H | i-Pr | $C_2H_5$ | 91.0–94.0 |
| II-10 | H | H | 4-OMe | H | i-Pr | $C_2H_5$ | 78.0–78.5 |
| II-11 | H | H | 4-OMe | H | i-Pr | $C_2H_5$ | 75.0–78.0 |
| II-12 | 6-Cl | H | 2-Cl | H | i-Pr | $C_2H_5$ | oil |
| II-13 | H | H | 4-$CF_3$ | H | i-Pr | $C_2H_5$ | 78.0–83.0 |
| II-14 | H | H | 3-Me | 4-F | i-Pr | $C_2H_5$ | 66.0–71.0 |
| II-15 | H | H | 3-Me | 5-Me | i-Pr | $C_2H_5$ | oil |
| II-16 | 6-OMe | 7-OMe | 4-F | H | i-Pr | $C_2H_5$ | 83.0–90.0 |
| II-17 | H | H | 4-F | H | $C_2H_5$ | $C_2H_5$ | 94.0–97.0 |
| II-18 | H | H | 4-F | H | n-Pr | $C_2H_5$ | oil |
| II-19 | 6-Cl | H | 4-F | H | i-Pr | $C_2H_5$ | 111.0–113.5 |
| II-20 | H | H | 4-F | H | c-Pr | $C_2H_5$ | 91.0–93.0 |
| II-21 | H | H | 4-OPh | H | i-Pr | $C_2H_5$ | 121.0–125.0 |
| II-22 | 6-Cl | 8-Cl | 4-F | H | i-Pr | $C_2H_5$ | oil |
| II-23 | 6-Cl | H | H | H | Ph | $C_2H_5$ | oil |
| II-24 | 6-Cl | H | H | H | c-Pr | $C_2H_5$ | 69.0–71.0 |
| II-25 | H | H | 4-F | H | sec-Bu | $C_2H_5$ | oil |
| II-26 | 6-Me | H | 4-F | H | i-Pr | $C_2H_5$ | oil |
| II-27 | 6-OMe | 7-OMe | 4-F | H | c-Pr | $C_2H_5$ | oil |

II-7

H—NMR (in $CDCl_3$) δ ppm: 1.21(t, 3H, J=7 Hz), 1.32(d, 6H, J=6 Hz), 2.2–2.4(m, 2H), 2.5–2.7(m, 1H), 3.28(s, 1H), 3.34(Heptaplet, 1H, J=6 Hz), 4.08(q, 2H, J=7 Hz), 4.3–4.6(m, 1H), 5.28(dd, 1H, J=6 Hz, J=15 Hz), 6.53(dd, 1H, J=1.5 Hz, J=15 Hz), 6.9–8.0(m, 8H).

II-12

H—NMR (in $CDCl_3$) δ ppm: 1.25(t, 3H, J=7 Hz), 1.33(d, 6H, J=6 Hz), 2.2–2.4(m, 2H), 2.5–2.8(m, 1H), 3.32(s, 2H), 3.38(Heptaplet, 1H, J=6 Hz), 4.13(q, 2H, J=7 Hz), 4.2–4.6(m, 1H), 5.34(dd, 1H, J=6 Hz, J=15 Hz), 6.53(dd, 1H, J=1.5 Hz, J=15 Hz), 7.0–8.0(m, 7H).

II-15

H—NMR (in $CDCl_3$) δ ppm: 1.23(t, 3H, J=7 Hz), 1.35(d, 6H, J=6 Hz), 2.2–2.4(m, 2H), 2.31(s, 6H), 2.6–2.8(m, 1H), 3.32(s, 2H), 3.35(Heptaplet, 1H, J=6 Hz), 4.12(q, 2H, J=7 Hz), 4.3–4.7(m, 1H), 5.30(dd, 1H, J=6 Hz, J=16 Hz), 6.51(dd, 1H, J=1 Hz, J=16 Hz), 6.7–8.0(m, 7H).

II-18

H—NMR (in $CDCl_3$) δ ppm: 1.00(t, 3H, J=7 Hz), 1.26(t, 3H, J=7 Hz), 1.6–2.3(m, 2H), 2.42(d, 2H, J=6 Hz), 2.6–3.2(m, 3H), 3.35(s, 2H), 4.11(q, 2H, J=7 Hz), 4.3–4.7(m, 1H), 5.27(dd, 1H, J=6 Hz, J=16 Hz), 6.46(dd, 1H, J=1.5 Hz, J=16 Hz), 6.9–8.0(m, 8H).

II-22

H—NMR (in $CDCl_3$) δ ppm: 1.26(t, 3H, J=7 Hz), 1.33(d, 6H, J=6 Hz), 2.43(d, 2H, J=6 Hz), 2.6–2.9(m, 1H), 3.36(s, 2H), 3.44(Heptaplet, 1H, J=6 Hz), 4.13(q, 2H, J=7 Hz), 4.3–4.7(m, 1H), 5.30(dd, 1H, J=6 Hz, J=16 Hz), 6.53(dd, 1H, J=1.5 Hz, J=16 Hz), 7.0–7.6(m, 6H).

II-23

H—NMR (in $CDCl_3$) δ ppm: 1.23(t, 3H, J=7 Hz), 2.21(d, 2H, J=6 Hz), 2.4–2.6(m, 1H), 3.25(s, 2H), 4.09(q, 2H, J=7 Hz), 4.1–4.4(m, 1H), 5.08(dd, 1H, J=6 Hz, J=16 Hz), 6.26(dd, 1H, J=1.5 Hz, J=16 Hz), 7.0~8.0 (m, 13H).

II-25

H—NMR (in $CDCl_3$) δ ppm: 0.96(d, 6H, J=6 Hz), 1.26(t, 3H, J=7 Hz), 1.3–2.4(m, 1H), 2.43(d, 2H, J=6 Hz), 2.6–2.9(m, 1H), 2.88(d, 2H, J=7 Hz), 3.36(s, 2H), 4.14(q, 2H, J=7 Hz), 4.3–4.7(m, 1H), 5.0–5.5(m, 1H), 6.3–6.7(m, 1H), 6.9–8.1(m, 8H).

II-26

H—NMR (in $CDCl_3$) δ ppm: 1.25(t, 3H, J=7 Hz), 1.32(d, 6H, J=6 Hz), 2.32(s, 3H), 2.39(d, 2H, J=7 Hz), 2.6–3.1(m, 1H), 3.36(s, 2H), 3.41(Heptaplet, 1H, J=6 Hz), 4.11(q, 2H, J=7 Hz), 4.3–4.7(m, 1H), 5.0–5.5(m, 1H), 6.3–6.7(m, 1H), 6.8–7.9(m, 7H).

II-27

H—NMR (in $CDCl_3$) δ ppm: 0.8–1.5(m, 4H), 1.26(t, 3H, J=7 Hz), 2.0–2.9(m, 4H), 3.42(s, 2H), 3.71(s, 3H), 4.00(s, 3H), 4.20(q, 2H, J=7 Hz), 4.4–4.8(m, 1H), 5.3–5.8(m, 1H), 6.4–6.9(m, 1H), 6.58(s, 1H), 7.0–7.5(m, 5H).

In the same manner as in Example 1-g, compounds I-12 to I-127 were prepared.

TABLE 10

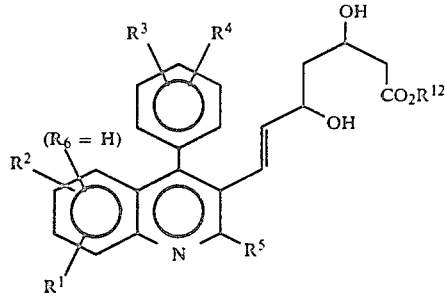

| Compound | $R^1$ | $R^2$ | $R^3$ | $R^4$ | $R^5$ | $R^{12}$ | m.p.(°C.) Mass spectrum |
|---|---|---|---|---|---|---|---|
| I-12 | H | H | 4-F | H | $CH_3$ | $C_2H_5$ | oil M/e 423.292 264,249 |
| I-13 | H | H | H | H | $CH_3$ | $C_2H_5$ | 92–105 |
| I-14 | H | H | H | H | i-Pr | $C_2H_5$ | 97–100 |
| I-15 | 6-Cl | H | H | H | $CH_3$ | $C_2H_5$ | oil |

TABLE 10-continued

I-1

Structure: Quinoline with R³, R⁴ on phenyl ring, R¹, R² on quinoline, R⁵ at position, R⁶=H, and side chain —CH=CH—CH(OH)—CH₂—CH(OH)—CH₂—$CO_2R^{12}$

| Compound | $R^1$ | $R^2$ | $R^3$ | $R^4$ | $R^5$ | $R^{12}$ | m.p.(°C.) Mass spectrum |
|---|---|---|---|---|---|---|---|
| I-16 | 6-Cl | H | H | H | i-Pr | $C_2H_5$ | oil |
| I-17 | H | H | 2-F | H | i-Pr | $C_2H_5$ | oil |
| I-18 | 7-Me | H | H | H | i-Pr | $C_2H_5$ | oil |
| I-19 | H | H | 4-Cl | H | i-Pr | $C_2H_5$ | 98–104 |
| I-110 | H | H | 4-OMe | H | i-Pr | $C_2H_5$ | 94–98 |
| I-111 | H | H | 4-Me | H | i-Pr | $C_2H_5$ | 79–85 |
| I-112 | 6-Cl | H | 2-Cl | H | i-Pr | $C_2H_5$ | oil |
| I-113 | H | H | 4-$CF_3$ | H | i-Pr | $C_2H_5$ | 117–128 |
| I-114 | H | H | 3-Me | 4-F | i-Pr | $C_2H_5$ | 85–92 |
| I-115 | H | H | 3-Me | 5-Me | i-Pr | $C_2H_5$ | oil |
| I-116 | 6-OMe | 7-OMe | 4-F | H | i-Pr | $C_2H_5$ | gum |
| I-117 | H | H | 4-F | H | $C_2H_5$ | $C_2H_5$ | oil |
| I-118 | H | H | 4-F | H | n-Pr | $C_2H_5$ | oil |
| I-119 | 6-Cl | H | 4-F | H | i-Pr | $C_2H_5$ | 79–82 |
| I-120 | H | H | 4-F | H | c-Pr | $C_2H_5$ | 100–104 |
| I-121 | H | H | 4-OPh | H | i-Pr | $C_2H_5$ | oil |
| I-122 | 6-Cl | 8-Cl | 4-F | H | i-Pr | $C_2H_5$ | 133–143 |
| I-123 | 6-Cl | H | H | H | Ph | $C_2H_5$ | gum |
| I-124 | 6-Cl | H | H | H | c-Pr | $C_2H_5$ | oil |
| I-125 | H | H | 4-F | H | sec-Bu | $C_2H_5$ | oil |
| I-126 | 6-Me | H | 4-F | H | i-Pr | $C_2H_5$ | oil |
| I-127 | 6-OMe | 7-OMe | 4-F | H | c-Pr | $C_2H_5$ | gum |

I-17

H—NMR (in $CDCl_3$) δ ppm: 1.29(t, 3H, J=7 Hz), 1.40(d, 6H, J=6 Hz), 1.4–1.7(m, 2H), 2.3–2.5(m, 2H), 2.9–3.2(m, 1H), 3.49(Heptaplet,1H,J=6 Hz), 3.5–3.8(m, 1H), 3.9–4.5(m, 2H), 4.20(q, 2H, J=7 Hz), 5.2–5.7(m, 1H), 6.5–6.9(m, 1H), 7.0–8.2(m, 8H).

I-18

H—NMR (in $CDCl_3$) δ ppm: 1.0–1.4(m, 2H), 1.31(t, 3H, J=7 Hz), 1.39(d, 6H, J=6 Hz), 2.3–2.5(m, 2H), 2.52(s, 3H), 3.1–3.4(m, 1H), 3.48(Heptaplet,1H,J=6 Hz), 3.5–3.8(m, 1H), 3.8–4.1(m, 1H), 4.20(q, 2H, J=7 Hz), 4.2–4.5(m, 1H), 5.2–5.6(m, 1H), 6.4–6.8(m, 1H), 7.0–8.0(m, 8H).

I-19

H—NMR (in $CDCl_3$) δ ppm: 1.29(t, 3H, J=7 Hz), 1.38(d, 6H, J=6 Hz), 1.4–1.8(m, 2H), 2.3–2.5(m, 2H), 3.2–3.4(m, 1H), 3.49(Heptaplet,1H,J=6 Hz), 3.6–3.8(m, 1H), 3.9–4.2(m, 1H), 4.20(q, 2H, J=7 Hz), 4.3–4.5(m, 1H), 5.2–5.5(m, 1H), 6.5–6.8(m, 1H), 7.0–8.2(m, 8H).

I-110

H—NMR (in $CDCl_3$) δ ppm: 1.29(t, 3H, J=7 Hz), 1.40(d, 6H, J=6 Hz), 1.5–1.6(m, 2H), 2.3–2.5(m, 2H), 2.8–3.0(m, 1H), 3.4–3.6(m, 1H), 3.52(Heptaplet,1H,J=6 Hz), 3.88(s, 3H), 3.9–4.1(m, 1H), 4.20(q, 2H, J=7 Hz), 4.3–4.5(m, 1H), 5.3–5.5(m, 1H), 6.5–6.7(m, 1H), 6.9–8.1(m, 8H).

I-111

H—NMR (in $CDCl_3$) δ ppm: 1.30(t, 3H, J=7 Hz), 1.3–1.5(m, 2H), 1.39(d, 6H, J=6 Hz), 2.3–2.5(m, 2H), 2.43(s, 3H), 2.8–3.0(m, 1H), 3.50(Heptaplet,1H,J=6 Hz), 3.5–3.7(m, 1H), 3.9–4.2(m, 1H), 4.19(q, 2H, J=7 Hz), 4.2–4.5(m, 1H), 5.2–5.6(m, 1H), 6.4–6.8(m, 1H), 6.9–8.2(m, 8H).

I-112

H—NMR (in $CDCl_3$) δ ppm: 1.30(t, 3H, J=7 Hz), 1.3–1.6(m, 2H), 1.37(d, 6H, J=6 Hz), 2.3–2.5(m, 2H), 2.9–3.2(m, 1H), 3.47(Heptaplet,1H,J=6 Hz), 3.5–3.8(m, 1H), 3.9–4.1(m, 1H), 4.19(q, 2H, J=7 Hz), 4.2–4.5(m, 1H), 5.3–5.7(m, 1H), 6.5–6.8(m, 1H), 7.1–8.1(m, 7H).

I-113

H—NMR (in $CDCl_3$) δ ppm: 1.0–1.3(m, 2H), 1.30(t, 3H, J=7 Hz), 1.40(d, 6H, J=6 Hz), 2.3–2.4(m, 2H), 3.3–3.5(m, 1H), 3.49(Heptaplet,1H,J=6 Hz), 3.6–3.7(m, 1H), 3.9–4.1(m, 1H) 4.18(q, 2H, J=7 Hz), 4.2–4.5(m, 1H) 5.1–5.5(m, 1H), 6.5–6.8(m, 1H) 7.2–8.2(m, 8H).

I-114

H—NMR (in $CDCl_3$) δ ppm: 1.2–1.4(m, 2H), 1.30(t, 3H, J=7 Hz), 1.39(d, 6H, J=6 Hz), 2.32(bs, 3H), 2.3–2.5(m, 2H), 3.0–3.3(m, 1H), 3.50(Heptaplet,1H,J=6 Hz), 3.6–3.8(m, 1H), 3.8–4.1(m, 1H), 4.20(q, 2H, J=7 Hz), 4.3–4.6(m, 1H), 5.2–5.6(m, 1H), 6.5–6.8(m, 1H), 7.0–8.2(m, 7H).

I-115

H—NMR (in $CDCl_3$) δ ppm: 1.1–1.4(m, 2H), 1.30(t, 3H, J=7 Hz), 1.40(d, 6H, J=6 Hz), 2.2–2.5(m, 2H), 2.35(s, 6H), 2.7–3.1(m, 1H), 3.51(Heptaplet,1H,J=6 Hz), 3.6–3.7(m, 1H), 3.8–4.1(m, 1H), 4.20(q, 2H, J=7 Hz), 4.2–4.6(m, 1H), 5.2–5.6(m, 1H), 6.4–6.8(m, 1H), 6.8–8.2(m, 7H).

I-116

H—NMR (in $CDCl_3$) δ ppm: 1.30(t, 3H, J=7 Hz), 1.37(d, 6H, J=6 Hz), 1.5–1.8(m, 2H), 2.3–2.5(m, 2H), 2.9–3.2(m, 1H), 3.46(Heptaplet,1H,J=6 Hz), 3.6–3.8(m, 1H), 3.75(s, 3H), 3.9–4.1(m, 1H), 4.07(s, 3H), 4.20(q, 2H, J=7 Hz), 4.2–4.5(m, 1H), 5.1–5.5(m, 1H), 6.4–6.8(m, 2H), 7.1–7.5(m, 5H).

I-117

H—NMR (in $CDCl_3$) δ ppm: 1.30(t, 3H, J=7 Hz), 1.37(t, 3H, J=7 Hz), 1.4–1.7(m, 2H), 2.2–2.6(m, 2H), 2.8–3.2(m, 3H), 3.6–3.9(m, 1H), 3.9–4.7(m, 4H), 5.2–5.7(m, 1H), 6.3–6.7(m, 1H), 7.0–8.2(m, 8H).

I-118

H—NMR (in $CDCl_3$) δ ppm: 1.01(t, 3H, J=7 Hz), 1.27(t, 3H, J=7 Hz), 1.4–2.1(m, 4H), 2.3–2.6(m, 2H), 2.8–3.3(m, 3H), 3.6–3.8(m, 1H), 3.9–4.1(m, 1H), 4.18(q, 2H, J=7 Hz), 4.2–4.5(m, 1H), 5.2–5.6(m, 1H), 6.4–6.7(m, 1H), 7.0–8.1(m, 8H).

I-119

H—NMR (in $CDCl_3$) δ ppm: 1.2–1.5(m, 2H), 1.31(t, 3H, J=7 Hz), 1.37(d, 6H, J=7 Hz), 2.3–2.6(m, 2H), 3.0–3.4(m, 1H), 3.49(Heptaplet,1H,J=6 Hz), 3.6–3.8(m, 1H), 3.8–4.2(m, 1H), 4.20(q, 2H, J=7 Hz), 4.3–4.5(m, 1H), 5.2–5.6(m, 1H), 6.4–6.8(m, 1H), 7.0–8.1(m, 7H).

I-120

H—NMR (in $CDCl_3$) δ ppm: 0.8–1.8(m, 6H), 1.30(t, 3H, J=7 Hz), 2.1–2.6(m, 3H), 2.9–3.3(m, 1H), 3.4–3.7(m, 1H), 3.8–4.6(m, 2H), 4.20(q, 2H, J=7 Hz), 5.4–5.8(m, 1H), 6.4–6.8(m, 1H), 6.8–8.0(m, 8H),

I-121

H—NMR (in $CDCl_3$) δ ppm: 1.29(t, 3H, J=7 Hz), 1.39(d, 6H, J=6 Hz), 1.4–1.9(m, 2H), 2.3–2.5(m, 2H), 2.7–3.2(m, 1H), 3.51(Heptaplet,1H,J=6 Hz), 3.6–3.8(m, 1H), 3.9–4.2(m, 1H), 4.19(q, 2H, J=7 Hz), 4.3–4.6(m, 1H), 5.2–5.6(m, 1H), 6.4–6.8(m, 1H), 6.9–8.2(m, 13H).

I-122

H—NMR (in $CDCl_3$) δ ppm: 1.1–1.8(m, 2H), 1.31(t, 3H, J=7 Hz), 1.41(d, 6H, J=6 Hz), 2.3–2.5(m, 2H), 2.9–3.4(m, 1H), 3.50(Heptaplet,1H,J=6 Hz), 3.6–3.8(m, 1H), 3.9–4.5(m, 2H), 4.20(q, 2H, J=7 Hz), 5.2–5.6(m, 1H), 6.4-6.8(m, 1H), 7.1-7.3(m, 5H), 7.72(d, 1H, J=6 Hz).

In the same manner as in Example 2, compounds I-52 to I-527 were prepared.

TABLE 11

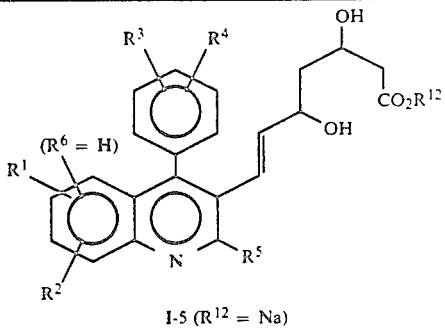

I-5 ($R^{12}$ = Na)

| Compound | $R^1$ | $R^2$ | $R^3$ | $R^4$ | $R^5$ | $R^{12}$ | m.p. (°C.) |
|---|---|---|---|---|---|---|---|
| I-52 | H | H | 4-F | H | $CH_3$ | Na | 138-142 (decomposed) |
| I-53 | H | H | H | H | $CH_3$ | Na | 130-132 (decomposed) |
| I-54 | H | H | H | H | i-Pr | Na | 196-197 (decomposed) |
| I-55 | 6-Cl | H | H | H | $CH_3$ | Na | 211-215 (decomposed) |
| I-56 | 6-Cl | H | H | H | i-Pr | Na | 195-198 (decomposed) |
| I-57 | H | H | 2-F | H | i-Pr | Na | 193-201 (decomposed) |
| I-58 | 7-Me | H | H | H | i-Pr | Na | 170-175 (decomposed) |
| I-59 | H | H | 4-Cl | H | i-Pr | Na | 193-202 (decomposed) |
| I-510 | H | H | 4-OMe | H | i-Pr | Na | 178-193 (decomposed) |
| I-511 | H | H | 4-Me | H | i-Pr | Na | 187-200 (decomposed) |
| I-512 | 6-Cl | H | 2-Cl | H | i-Pr | Na | 203-209 (decomposed) |
| I-513 | H | H | 4-$CF_3$ | H | i-Pr | Na | 200-212 (decomposed) |
| I-514 | H | H | 3-Me | 4-F | i-Pr | Na | 195-200 (decomposed) |
| I-515 | H | H | 3-Me | 5-Me | i-Pr | Na | 192-197 (decomposed) |
| I-516 | 6-OMe | 7-OMe | 4-F | H | i-Pr | Na | 239-245 (decomposed) |
| I-517 | H | H | 4-F | H | $C_2H_5$ | Na | 230-237 (decomposed) |
| I-518 | H | H | 4-F | H | n-Pr | Na | 193-200 (decomposed) |
| I-519 | 6-Cl | H | 4-F | H | i-Pr | Na | 193-198 (decomposed) |
| I-520 | H | H | 4-F | H | c-Pr | Na | 197-199 (decomposed) |
| I-521 | H | H | 4-OPh | H | i-Pr | Na | 180-189 (decomposed) |
| I-522 | 6-Cl | 8-Cl | 4-F | H | i-Pr | Na | 183-187 (decomposed) |
| I-523 | 6-Cl | H | H | H | Ph | Na | 190-196 (decomposed) |
| I-524 | 6-Cl | H | H | H | c-Pr | Na | 204-210 (decomposed) |
| I-525 | H | H | 4-F | H | sec-Bu | Na | — |
| I-526 | 6-Me | H | 4-F | H | i-Pr | Na | 204-208 (decomposed) |
| I-527 | 6-OMe | 7-OMe | 4-F | H | c-Pr | Na | 234-238 (decomposed) |

I-123

H—NMR (in $CDCl_3$) δ ppm: 0.8-1.5(m, 2H), 1.29(t, 3H, J=7 Hz), 2.2-2.4(m, 2H), 2.6-2.9(m, 1H), 3.2-3.6(m, 1H), 3.7-4.3(m, 2H), 4.17(q, 2H, J=7 Hz), 5.0-5.4(m, 1H), 6.1-6.5(m, 1H), 7.0-8.2(m, 13H).

I-124

H—NMR (in $CDCl_3$) δ ppm: 0.8-1.8(m, 6H), 1.29(t, 3H, J=7 Hz), 2.2-2.6(m, 3H), 2.8-3.2(m, 1H), 3.3-3.7(m, 1H), 3.9-4.5(m, 2H), 4.19(q, 2H, J=7 Hz), 5.4-5.8(m, 1H), 6.5-6.8(m, 1H), 7.1-8.0(m, 8H).

I-125

H—NMR (in $CDCl_3$) δ ppm: 0.94(d, 6H, J=6 Hz), 1.0-1.7(m, 3H), 1.27(t, 3H, J=7 Hz), 1.9-2.5(m, 3H), 2.90(d, 2H, J=7 Hz), 3.3-4.4(m, 3H), 4.12(q, 2H, J=7 Hz), 5.0-5.5(m, 1H), 6.2-6.7(m, 1H), 6.9-8.0(m, 8H).

I-126

H—NMR (in $CDCl_3$) δ ppm: 1.0-1.6(m, 3H), 1.21(t, 3H, J=7 Hz), 1.34(d, 6H, J=6 Hz), 2.34(s, 3H), 2.37(d, 2H, J=7 Hz), 2.9-3.7(m, 2H), 3.8-4.5(m, 2H), 4.15(q, 2H, J=7 Hz), 5.0-5.5(m, 1H), 6.3-6.7(m, 1H), 6.9-8.0(m, 7H).

I-127

H—NMR (in $CDCl_3$) δ ppm: 0.8-1.9(m, 8H), 1.29(t, 3H, J=7 Hz), 2.1-2.6(m, 3H), 2.8-3.2(m, 1H), 3.72(s, 3H), 4.02(s, 3H), 4.19(q, 2H, J=7 Hz), 4.3-4.6(m, 1H), 5.4-5.8(m, 1H), 6.4-6.8(m, 1H), 6.56(s, 1H), 7.0-7.4(m, 5H).

I-57

H—NMR (in DMSO-$d^6$) δ ppm: 0.9-1.2(m, 2H), 1.37(d, 6H, J=7 Hz), 1.6-2.1(m, 2H), 3.48(Heptaplet,1H,J=6 Hz), 3.7-4.3(m, 4H), 5.3-5.6(m, 1H), 6.4-6.7(m, 1H), 7.1-8.1(m, 8H).

I-58

H—NMR (in DMSO-$d^6$) δ ppm: 0.9-1.2(m, 2H), 1.31(d, 6H, J=7 Hz), 1.7-2.2(m, 2H), 2.50(s, 3H), 3.3-4.5(m, 5H), 5.2-5.6(m, 1H), 6.3-6.6(m, 1H), 7.1-7.9(m, 8H).

I-59

H—NMR (in DMSO-$d^6$) δ ppm: 0.9-1.3(m, 2H), 1.33(d, 6H, J=7 Hz), 1.6-2.2(m, 2H), 3.48(Heptaplet,1H,J=7 Hz), 3.5-4.6(m, 4H), 5.2-5.6(m, 2H), 6.3-6.6(m, 1H), 7.1-8.1(m, 8H).

I-510

H—NMR (in DMSO-$d^6$) δ ppm: 1.0-1.3(m, 2H), 1.32(d, 6H, J=7 Hz), 1.6-2.2(m, 2H), 3.0-3.8(m, 4H), 3.86(s, 3H), 4.0-4.3(m, 1H), 5.3-5.6(m, 1H), 6.3-6.6(m, 1H) 6.9-8.1(m, 8H).

I-511

H—NMR (in DMSO-$d^6$) δ ppm: 0.9-1.3(m, 2H), 1.33(d, 6H, J=7 Hz), 1.7-2.1(m, 2H), 2.41(s, 3H), 3.2-4.3(m, 5H), 5.3-5.6(m, 1H), 6.3-6.6(m, 1H), 7.0-8.3(m, 8H).

I-512

H—NMR (in DMSO-d⁶) δ ppm: 0.9–1.3(m, 2H), 1.33(d, 6H, J=7 Hz), 1.6–2.2(m, 2H), 3.1–3.8(m, 3H), 3.48(Heptaplet,1H,J=7 Hz), 3.9–4.2(m, 1H), 5.3–5.7(m, 1H), 6.3–6.7(m, 1H), 7.0–8.1(m, 7H).

I-513

H—NMR (in DMSO-d⁶) δ ppm: 0.8–1.3(m, 2H), 1.34(d, 6H, J=7 Hz), 1.6–2.2(m, 2H), 2.7–3.9(m, 3H), 3.49(Heptaplet,1H,J=7 Hz), 3.9–4.3(m, 1H), 5.2–5.6(m, 1H), 6.3–6.7(m, 1H) 7.1–8.1(m, 8H).

I-514

H—NMR (in DMSO-d⁶) δ ppm: 0.9–1.3(m, 2H), 1.35(d, 6H, J=7 Hz), 1.7–2.1(m, 2H), 2.30(d, 3H, J=2 Hz), 3.0–3.8(m, 3H), 3.51(Heptaplet,1H,J=7 Hz), 3.9–4.3(m, 1H), 5.3–5.6(m, 1H), 6.3–6.6(m, 1H), 6.9–8.1(m, 7H).

II-515

H—NMR (in DMSO-d⁶) δ ppm: 1.0–1.2(m, 2H), 1.35(d, 6H, J=7 Hz), 1.6–2.2(m, 2H), 2.35(s, 6H), 3.0–3.8(m, 3H), 3.51(Heptaplet,1H,J=7 Hz), 4.0–4.3(m, 1H), 5.3–5.6(m, 1H), 6.3–6.6(m, 1H), 6.8–8.0(m, 7H).

I-516

H—NMR (in DMSO-d⁶) δ ppm: 0.9–1.3(m, 2H), 1.31(d, 6H, J=7 Hz), 1.7–2.0(m, 2H), 3.2–3.7(m, 4H), 3.62(s, 3H), 3.9–4.2(m, 1H), 3.94(s, 3H), 5.1–5.5(m, 1H), 6.2–6.6(m, 1H), 7.0–7.5(m, 6H).

I-517

H—NMR (in DMSO-d⁶) δ ppm: 0.9–1.5(m, 2H), 1.34(t, 3H, J=7 Hz), 1.6–2.2(m, 2H), 2.7–3.4(m, 4H), 3.6–4.3(m, 2H), 5.2–5.7(m, 1H), 6.1–6.6(m, 1H), 6.9–8.1(m, 8H).

I-518

H—NMR (in DMSO-d⁶) δ ppm: 0.8–1.3(m, 2H), 1.01(t, 3H, J=7 Hz), 1.6–2.1(m, 4H), 2.7–3.8(m, 5H), 3.9–4.3(m, 1H), 5.2–5.7(m, 1H), 6.3–6.6(m, 1H), 7.1–8.1(m, 8H).

I-519

H—NMR (in DMSO-d⁶) δ ppm: 0.9–1.3(m, 2H), 1.33(d, 6H, J=7 Hz), 1.6–2.2(m, 2H), 2.9–3.9(m, 3H), 3.49(Heptaplet,1H,J=7 Hz), 4.0–4.3(m, 1H), 5.3–5.6(m, 1H), 6.3–6.6(m, 1H), 7.2–8.1(m, 7H).

I-520

H—NMR (in DMSO-d⁶) δ ppm: 0.8–1.5(m, 6H), 1.7–2.2(m, 2H), 2.3–2.7(m, 1H), 3.0–3.9(m, 3H), 4.0–4.3(m, 1H), 5.5–5.8(m, 1H), 6.4–6.7(m, 1H), 7.2–8.0(m, 8H).

I-521

H—NMR (in DMSO-d⁶) δ ppm: 0.9–1.5(m, 2H), 1.36(d, 6H, J=7 Hz), 1.7–2.3(m, 2H), 3.0–3.9(m, 3H), 3.50(Heptaplet,1H,J=6 Hz), 4.0–4.3(m, 1H), 5.2–5.6(m, 1H), 6.4–6.7(m, 1H), 7.0–8.1(m, 13H).

I-522

H—NMR (in DMSO-d⁶) δ ppm: 0.8–1.3(m, 2H), 1.37(d, 6H, J=7 Hz), 1.6–2.2(m, 2H), 3.1–3.9(m, 3H), 3.51(Heptaplet,1H,J=7 Hz), 4.0–4.3(m, 1H), 5.3–5.7(m, 1H), 6.3–6.7(m, 1H), 7.1–8.0(m, 6H).

I-523

H—NMR (in DMSO-d⁶) δ ppm: 0.8–1.4(m, 2H), 1.6–2.1(m, 2H), 2.9–3.7(m, 3H), 3.7–4.1(m, 1H), 5.1–5.4(m, 1H), 6.1–6.4(m, 1H), 7.1–8.2(m, 13H).

I-524

H—NMR (in DMSO-d⁶) δ ppm: 0.8–1.5(m, 5H), 1.6–2.2(m, 2H), 2.3–2.7(m, 2H), 3.0–3.8(m, 3H), 3.9–4.3(m, 1H), 5.4–5.8(m, 1H), 6.3–6.6(m, 1H), 7.0–8.0(m, 8H).

I-525

H—NMR (in DMSO-d⁶) δ ppm: 0.9–1.6(m, 2H), 0.96(d, 6H, J=6 Hz), 1.7–2.6(m, 3H), 2.89(d, 2H, J=7 Hz), 3.0–3.8(m, 3H), 3.9–4.2(m, 1H), 5.2–5.6(m, 1H), 6.2–6.6(m, 1H), 7.1–8.1(m, 8H).

I-526

H—NMR (in DMSO-d⁶) δ ppm: 1.30(d, 6H, J=7 Hz), 1.7–2.0(m, 2H), 2.34(s, 3H), 2.4–2.6(m, 1H), 3.0–3.3(m, 2H), 3.3–3.8(m, 3H), 3.9–4.2(m, 1H), 5.2–5.6(m, 1H), 6.3–6.6(m, 1H), 7.0–8.0(m, 7H).

I-527

H—NMR (in DMSO-d⁶) δ ppm: 0.7–1.5(m, 5H), 1.8–2.2(m, 2H), 2.2–2.6(m, 2H), 3.1–3.3(m, 2H), 3.59(s, 3H), 3.9–4.2(m, 2H), 3.91(s, 3H), 5.4–5.7(m, 1H), 6.3–6.6(m, 1H), 6.52(s, 1H), 7.0–7.4(m, 5H).

In the same manner as in Example 3, compounds I-22 to I-26 can be prepared.

TABLE 12

I-2

| Compound | R¹ | R² | R³ | R⁴ | R⁵ |
|---|---|---|---|---|---|
| I-22 | H | H | 4-F | H | CH₃ |
| I-23 | H | H | H | H | CH₃ |
| I-24 | H | H | H | H | i-Pr |
| I-25 | 6-Cl | H | H | H | CH₃ |
| I-26 | 6-Cl | H | H | H | i-Pr |

In the same manner as in Example 4, compounds I-32 to I-36 can be prepared.

TABLE 13

I-3

| Compound | R¹ | R² | R³ | R⁴ | R⁵ |
|---|---|---|---|---|---|
| I-32 | H | H | 4-F | H | CH₃ |
| I-33 | H | H | H | H | CH₃ |
| I-34 | H | H | H | H | i-Pr |
| I-35 | 6-Cl | H | H | H | CH₃ |
| I-36 | 6-Cl | H | H | H | i-Pr |

FORMULATION EXAMPLE 1

| Tablets | |
|---|---|
| Compound I-51 | 1.0 g |
| Lactose | 5.0 g |
| Crystal cellulose powder | 8.0 g |
| Corn starch | 3.0 g |
| Hydroxypropyl cellulose | 1.0 g |
| CMC-Ca | 1.5 g |
| Magnesium stearate | 0.5 g |

-continued

| Tablets | |
|---|---|
| Total | 20.0 g |

The above components were mixed by a usual method and then tabletted to produce 100 tablets each containing 10 mg of the active ingredient.

FORMULATION EXAMPLE 2

| Capsules | |
|---|---|
| Compound I-51 | 1.0 g |
| Lactose | 3.5 g |
| Crystal cellulose powder | 10.0 g |
| Magnesium stearate | 0.5 |
| Total | 15.0 g |

The above components were mixed by a usual method and then packed in No. 4 gelatin capsules to obtain 100 capsules each containing 10 mg of the active ingredient.

FORMULATION EXAMPLE 3

| Soft capsules | |
|---|---|
| Compound I-51 | 1.00 g |
| PEG (polyethylene glycol) 400 | 3.89 g |
| Saturated fatty acid triglyceride | 15.00 g |
| Peppermint oil | 0.01 g |
| Polysorbate 80 | 0.10 g |
| Total | 20.00 g |

The above components were mixed and packed in No. 3 soft gelatin capsules by a usual method to obtain 100 soft capsules each containing 10 mg of the active ingredient.

FORMULATION EXAMPLE 4

| Ointment | |
|---|---|
| Compound I-51 | 1.0 g (10.0 g) |
| Liquid paraffin | 10.0 g (10.0 g) |
| Cetanol | 20.0 g (20.0 g) |
| White vaseline | 68.4 g (59.4 g) |
| Ethylparaben | 0.1 g (0.1 g) |
| L-menthol | 0.5 g (0.5 g) |
| Total | 100.0 g |

The above components were mixed by a usual method to obtain a 1% (10%) ointment.

FORMULATION EXAMPLE 5

| Suppository | |
|---|---|
| Compound I-51 | 1.0 g |
| Witepsol H15* | 46.9 g |
| Witepsol W35* | 52.0 g |
| Polysorbate 80 | 0.1 g |
| Total | 100.0 g |

*Trademark for triglyceride compound

The above components were melt-mixed by a usual method and poured into suppository containers, followed by cooling for solidification to obtain 100 suppositories of 1 g each containing 10 mg of the active component.

FORMULATION EXAMPLE 6

| Injection formulation | |
|---|---|
| Compound I-51 | 1 mg |
| Distilled water for injection formulation | 5 ml |

The formulation is prepared by dissolving the compound in the distilled water whenever it is required.

FORMULATION EXAMPLE 7

| Granules | |
|---|---|
| Compound I-51 | 1.0 g |
| Lactose | 6.0 g |
| Crystal cellulose powder | 6.5 g |
| Corn starch | 5.0 g |
| Hydroxypropyl cellulose | 1.0 g |
| Magnesium stearate | 0.5 g |
| Total | 20.0 g |

The above components were granulated by a usual method and packaged to obtain 100 packages each containing 200 mg of the granules so that each package contains 10 mg of the active ingredient.

We claim:

1. A compound of the formula

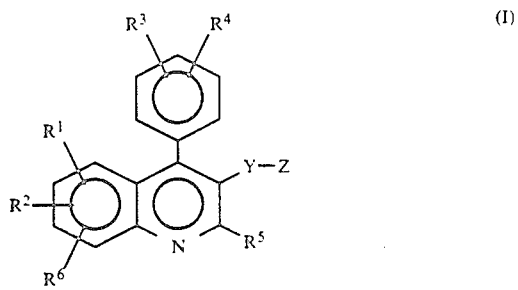

wherein $R^1$ and $R^2$ are ortho to each other and together form —$OCR^{15}R^{16}O$—, wherein $R^{15}$ and $R^{16}$ are independently H or $C_{1-3}$ alkyl; $R^3$, $R^4$ and $R^6$ are independently hydrogen, $C_{1-6}$ alkyl, $C_{1-6}$ cycloalkyl, $C_{1-3}$ alkoxy, n-butoxy, i-butoxy, sec-butoxy, $R^7R^8N$—, ($R^7$ and $R^8$ are independently hydrogen or $C_{1-3}$ alkyl), trifluoromethyl, trifluoromethoxy, difluoromethoxy, fluoro, chloro, bromo, phenyl, phenoxy, benzyloxy, hydroxy, trimethylsilyloxy, diphenyl-t-butylsilyloxy, hydroxymethyl or —$O(CH_2)_l OR^{19}$ (wherein $R^{19}$ is hydrogen or $C_{1-3}$ alkyl, and l is 1, 2 or 3); or when located at the ortho position to each other, $R_3$ and $R_4$ together form —CH=CH—CH=CH—; Y is —$CH_2$—, —$CH_2CH_2$—, CH=CH—, $CH_2$—CH=CH— or —CH=CH—$CH_2$—; and Z is —Q—$Ch_2WCH_2$—$CO_2R^{12}$,

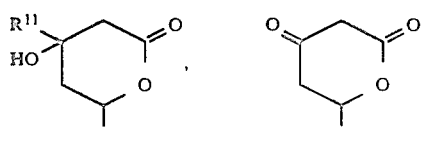

or

-continued

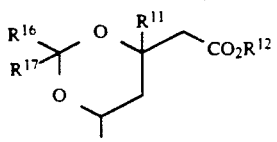

(where Q is —(CO)—, —C(OR$^{13}$)$_2$— or —CH(OH)—; W is —C(O)—, —C(OR$^{13}$)$_2$— or —C(R$^{11}$)(OH)—; R$^{11}$ is hydrogen or C$_{1-3}$ alkyl; R$^{12}$ is hydrogen or R$^{14}$ (wherein R$^{14}$ is physiologically hydrolyzable alkyl or M (wherein M is NH$_4$, sodium, potassium, ½ calcium or a hydrate of lower alkylamine, di-lower alkylamine or tri-lower alkylamine)); two R$^{13}$ are independently primary or secondary C$_{16}$ alkyl; or two R$^{13}$ together form —(CH$_2$)$_2$— or (CH$_2$)$_3$—; R$^{17}$ and R$^{18}$ are independently hydrogen or C$_{1-3}$ alkyl; and R$^5$ is hydrogen, C$_{1-6}$ alkyl, C$_{2-3}$ alkenyl, C$_{3-6}$ cycloalkyl,

(wherein R$^9$ is hydrogen, C$_{1-4}$ alkyl, C$_{1-3}$ alkyl, fluoro, chloro, bromo trifluoromethyl), phenyl—(CH$_2$)$_n$CH(CH$_3$)—phenyl or phenyl—(CH$_2$)$_n$CH(CH$_3$)—phenyl (wherein n is 0, 1 or 2).

2. The compound of claim 1, wherein R$^1$ and R$^2$ together form methylenedioxy.

3. The compound of claim 2, wherein said methylenedioxy is attached to the quinoline moiety at positions 6 and 7 or 7 and 8.

4. The compound of claim 3, wherein R$^6$ is hydrogen.

5. The compound of claim 3, wherein R$^3$ is hydrogen.

6. The compound according to claim 1, which is (E)-3,5-dihydroxy-7-[4'-(4''-fluorophenyl)-6',7'-methylenedioxy-2'-(1'''-methylethyl)-quinolin-3'-yl]-hept-6-enoic acid, a lactone formed by the condensation of the carboxylic acid with hydroxy at the 5-position, or a sodium salt or C$_{1-3}$ alkyl ester of the carboxylic acid.

7. The compound according to claim 1, which is (E)-3,5-dihydroxy-7-[4'-(4''-fluorophenyl)-7',8'-methylenedioxy-2'-(1'''-methylethyl)-6'-chloro-6'-chloro-quinolin-3'-yl]-hept-6-enoic acid, a lactone formed by the condensation of the carboxylic acid with hydroxy at the 5-position, or a sodium salt or C$_{1-3}$ alkyl ester of the carboxylic acid.

8. The compound according to claim 1, which is (E)-3,5-dihydroxy-7-[2'-cyclopropyl-4'-(4''-fluorophenyl)-6',7'-methylenedioxy-quinolin-3'-yl]-hept-6-enoic acid, a lactone formed by the condensation of the carboxylic acid with hydroxy at the 5-position, or a sodium salt or C$_{1-3}$ alkyl ester of the carboxylic acid.

9. The compound according to claim 1, which is (E)-3,5-dihydroxy-7-[2'-cyclopropyl-4'-(4''-fluorophenyl)-7',8'-methylenedioxy-quinolin-3'-yl]-hept-6-enoic acid, a lactone formed by the condensation of the carboxylic acid with hydroxy at the 5-position, or a sodium salt or C$_{1-3}$ alkyl ester of the carboxylic acid.

10. A method for treating hyperlipidemia, which comprises administering an effective amount of the compound of the formula I as defined in claim 1.

11. A method for treating hyperlipoproteinemia which comprises administering an effective amount of the compound of the formula I as defined in claim 1.

12. A method for treating atherosclerosis which comprises adminstering an effective amount of the compound of the formula I as defined in claim 1.

* * * * *